US012383502B2

(12) United States Patent
Kokkinis et al.

(10) Patent No.: US 12,383,502 B2
(45) Date of Patent: Aug. 12, 2025

(54) COLD-WATER-DISPERSIBLE CHEMICAL DELIVERY SYSTEM

(71) Applicant: PHARMAKO BIOTECHNOLOGIES PTY LIMITED, Cromer (AU)

(72) Inventors: George Kokkinis, Cromer (AU); Vaskor Bala, Dee Why (AU)

(73) Assignee: PHARMAKO BIOTECHNOLOGIES PTY LIMITED, Cromer (AU)

( * ) Notice: Subject to any disclaimer, the term of this patent is extended or adjusted under 35 U.S.C. 154(b) by 0 days.

(21) Appl. No.: 16/604,078

(22) PCT Filed: Apr. 13, 2018

(86) PCT No.: PCT/AU2018/050339
§ 371 (c)(1),
(2) Date: Oct. 9, 2019

(87) PCT Pub. No.: WO2018/187849
PCT Pub. Date: Oct. 18, 2018

(65) Prior Publication Data
US 2020/0155455 A1    May 21, 2020

(30) Foreign Application Priority Data
Apr. 13, 2017  (AU) ................. 2017901375

(51) Int. Cl.
| A61K 9/14 | (2006.01) |
| A23L 33/105 | (2016.01) |
| A23L 33/12 | (2016.01) |
| A23L 33/17 | (2016.01) |
| A61K 31/05 | (2006.01) |
| A61K 31/12 | (2006.01) |
| A61K 31/122 | (2006.01) |
| A61K 31/16 | (2006.01) |
| A61K 31/352 | (2006.01) |
| A61K 36/9066 | (2006.01) |
| A61K 47/02 | (2006.01) |

(52) U.S. Cl.
CPC ............ *A61K 9/14* (2013.01); *A23L 33/105* (2016.08); *A23L 33/12* (2016.08); *A23L 33/17* (2016.08); *A61K 9/145* (2013.01); *A61K 31/05* (2013.01); *A61K 31/12* (2013.01); *A61K 31/122* (2013.01); *A61K 31/16* (2013.01); *A61K 31/352* (2013.01); *A61K 36/9066* (2013.01); *A61K 47/02* (2013.01); *A23V 2002/00* (2013.01)

(58) Field of Classification Search
CPC .................. A61K 9/145; A61K 36/9066
See application file for complete search history.

(56) References Cited

U.S. PATENT DOCUMENTS

| 5,716,928 A * | 2/1998 | Benet .................. A61K 36/899 |
| | | 424/409 |
| 6,361,799 B1 | 3/2002 | Palkhiwala |
| 6,500,473 B1 | 12/2002 | Koehler et al. |
| 6,531,158 B1 | 3/2003 | Teng et al. |
| 6,682,761 B2 | 1/2004 | Pace et al. |
| 2003/0129253 A1 | 7/2003 | Milley et al. |
| 2005/0008581 A1 | 1/2005 | Parkhideh |
| 2006/0275358 A1 | 12/2006 | Lin |
| 2008/0219963 A1 | 9/2008 | Paolo et al. |
| 2009/0092727 A1 | 4/2009 | Perlman |
| 2013/0266703 A1* | 10/2013 | Hassan .................. B01F 23/20 |
| | | 366/144 |
| 2014/0044788 A1 | 2/2014 | Verma et al. |
| 2015/0024060 A1* | 1/2015 | Madhavi ................. A23L 33/12 |
| | | 514/733 |
| 2016/0166516 A1* | 6/2016 | Gannon ............... A61K 9/4858 |
| | | 514/679 |
| 2016/0213584 A1 | 7/2016 | Howe |

FOREIGN PATENT DOCUMENTS

| CN | 102451469 | 5/2012 |
| EP | 3165218 A1 | 5/2017 |
| WO | 2013/062425 | 5/2013 |
| WO | 2016/142745 | 9/2016 |
| WO | 2016/174004 | 11/2016 |
| WO | 2017/023341 | 2/2017 |
| WO | 2017045034 A1 | 3/2017 |

OTHER PUBLICATIONS

Written Opinion of the International Search Authority for International Application No. PCT/AU2018/050339 mailed Jun. 13, 2018, 6 pgs.

Changdeo, et al., "Physicochemical characterization and solubility enhancement studies of allopurinol solid dispersions," Brazilian Journal of Pharmaceutical Sciences, Jul./Sep. 2011, pp. 513-523, vol. 47, No. 3.

Yang, et al., "Use of the Co-grinding Method to Enhance the Dissolution Behavior or a Poorly Water-Soluble Drug: Generation of Solvent-Free Drug-Polymer Solid Dispersions," Chem. Pharm. Bull., 2012, pp. 837-845, vol. 60, No. 7.

Tran, et al., "Micromeritic properties and instrumental analysis of physical mixtures and solid dispersions with adsorbent containing losartan: Comparison of dissolution-differentiating factors," Power Technology, 2015, pp. 269-275, vol. 272, Elsevier B.V.

Vacondio, et al. Amino Acid Derivatives as Palmitoylethanolamide Prodrugs: Synthesis, In Vitro Metabolism and In Vio Plasma Profile in Rats, PLOS ONE, Jun. 8, 2015, 24 pages.

European Search Report for EP Patent Application No. 18784720.7 dated Jan. 12, 2021, 9 pages.

\* cited by examiner

*Primary Examiner* — Tigabu Kassa
(74) *Attorney, Agent, or Firm* — Lowenstein Sandler LLP

(57) ABSTRACT

The use of hydrophobic compounds for oral administration is limited due to the inability of the compounds to disperse in liquids. The present invention relates generally to a method of preparing compositions comprising hydrophobic compounds that can be dispersed in liquid. In particular, the method relates to combining a solid substance comprising a hydrophobic compound with a dispersing agent under high shear.

6 Claims, 11 Drawing Sheets

COLD-WATER-DISPERSIBLE CHEMICAL DELIVERY SYSTEM

TECHNICAL FIELD

The present invention relates generally to a method of preparing compositions comprising hydrophobic compounds dispersed in liquid. In particular, the method relates to combining a solid substance comprising a hydrophobic compound with a dispersing agent under high shear.

BACKGROUND ART

Any discussion of the prior art throughout the specification should in no way be considered as an admission that such prior art is widely known or forms part of common general knowledge in the field.

There are many solid compounds with industrial and therapeutic applications that present challenges due to their hydrophobicity and inability to disperse, and remain dispersed, in liquids. These compounds have broad reaching applications, and include proteins for the health supplement sector, and compounds with health benefits that may be used as nutraceuticals or conventional medicines.

Solid substances comprising hydrophobic compounds in the form of particles, crystals and/or globules have surfaces that have low wettability. This means that liquid does not adhere well to these surfaces, preventing the compound from being effectively coated with liquid. The exposure of these surfaces in water leads to the particles, crystals and globules aggregating and/or agglomerating to shield the hydrophobic surfaces from the water.

The use of hydrophobic compounds with health benefits as orally administrable drugs, nutraceuticals or supplements can be limited by the lack of wettability of the compounds in the aqueous environment of the digestive system. The low wettability inevitably leads to aggregation of the compounds. Aggregated compounds have severely diminished bioavailability when compared to compounds that remain dispersed as individual particles. Hydrophobic compounds are known to be poorly absorbed by the gastrointestinal (GI) tract. Consequently, in order to achieve any therapeutic benefit from such compounds, the dosing levels must be substantially increased.

The bioavailability of solid compounds can be increased by reducing the particle size of the compounds and/or reducing the direct contact between the hydrophobic surfaces of the particles, as it is this direct contact that encourages the particles to aggregate and clump. Such dispersion of individual particles also exposes a greater surface area of the compound, thereby increasing the potential for absorption and utilization of the compound during digestion.

Of interest when considering methods of improving the dispersion of hydrophobic compounds are solid plant and animal fats, protein supplements, and phytochemicals, especially those that are extracted and processed into powders. For example, the fatty acid ethanolamides (FAEs) have potential benefits for the treatment and improvement of inflammation, pain, innate immunity, gut health and appetite suppression. However, upon consumption, the bioavailability of the FAEs is low. In another example, many protein and dietary supplements rely on whey protein and casein, which can be very hydrophobic, resulting in poor mixing in water prior to consumption and reduced absorption during digestion.

Polyphenols are a large and diverse group of phytochemicals with purported roles in the treatment and prevention of cancer, cardiovascular disease and neurodegenerative disorders. While it is desirous to nutraceutical and pharmaceutical manufacturers to provide polyphenols as oral supplements and drugs, many are very hydrophobic and have low bioavailability due to their poor gastrointestinal absorption.

In order to increase bioavailability of hydrophobic compounds for oral administration, it is possible to use a system such as a Self-Microemulsifying Drug Delivery System (SMEDDS). The SMEDDS systems rely on intrinsic properties of the compounds to form microemulsions which may be taken up by the body at various stages of the digestive process. However, to achieve an emulsion that enhances bioavailability, the SMEDDS system can only be loaded to 20-30% by weight with the desired compound. Moreover, the systems are inherently better suited to liquids, such as oils, and are less appropriate for solid fats or hydrophobic compounds in the form of powders.

It would therefore be advantageous to provide methods that allows for a higher loading of active compound(s) in compositions, especially orally administrable compositions, allowing for more efficient delivery of a compound and thus increased bioavailability. It would also be advantageous to be able to reduce the amount of an active compound that must be consumed in order to achieve a desired level of absorption during digestion.

It is an objective of the present invention to overcome or ameliorate at least one of the disadvantages of the prior art treatments, or to provide a useful alternative.

SUMMARY OF THE INVENTION

The present inventors have surprisingly found that when solid hydrophobic compounds are combined with small amounts of dispersing agents under high shear forces, the treated compound is more easily dispersed in water. The dispersion of individual particles exposes a greater surface area of the compound. In the case of compounds that are for oral consumption, in one or more embodiments, the enhanced dispersibility is accompanied by an increase in bioavailability of the compound because of the increased potential for absorption and utilization of the compound during digestion (see FIG. 1).

Accordingly, in a first aspect of the invention, there is provided a method of preparing a liquid dispersible composition comprising a hydrophobic compound and a dispersing agent, the method comprising the step of combining a solid substance comprising the hydrophobic compound with the dispersing agent whilst applying a shear force.

The solid substance may be any substance comprising at least one target hydrophobic compound, the hydrophobic compound being made up of particles that have a substantially non-wettable surface. The substance may contain other compounds or components, and these other compounds or components may or may not be hydrophobic. Alternatively, the substance may be a relatively pure preparation of only the target hydrophobic compound(s). The term "particle" refers to any small piece or fragment of a solid and encompasses within its meaning a crystal, grain, globule and the like. In embodiments of the invention, the solid substance is a powder made up of dry particles produced by grinding a solid. That the solid substance has non-wettable or poorly-wettable surfaces may be evidenced by the inability of the substance to effectively disperse in water at room temperature (i.e. when added to water, the substance substantially floats on top of the water or is poorly dispersed in the water, see FIG. 2).

Generally, the dispersing agent is a compound or composition which, when present on the surface of particles of the solid substance, increases the wettability of the solid substance comprising the hydrophobic compound, thereby improving dispersion of the substance in liquid. A liquid-dispersible solid substance will separate relatively uniformly in a liquid, without significant observable aggregation and/or agglomeration. The liquid may be water or a heterogenous liquid such as a biological fluid (i.e., gastric juices, digestive fluids and/or lubricants), or an industrial liquid (i.e., a base for a drinkable food product) or a pharmaceutical liquid (i.e., a base or buffer for an orally administrable liquid formulation or capsule formulation).

The dispersing agent may also generate repulsive forces between the particles. A particle with good wettability will disperse in a liquid more readily than a particle with poor wettability. Repulsive forces between these particles can help maintain the dispersion of the particles in the liquid by discouraging aggregation and agglomeration of the particles. For example, the dispersing agent may comprise positive charges that are present on the surface of particles of the solid substance comprising the hydrophobic compound after the method of the present invention. Particles in the liquid dispersible composition produced by the method of the invention with a net positive charge would repel each other, thereby preventing aggregation between said positively charged particles.

The wettability of the solid can be measured by the contact angle that liquid drops form on the surface of a solid (see FIG. 3). A smaller contact angle indicates better wetting. The skilled addressee would appreciate that a contact angle below 90 degrees for a surface is considered to have good wettability. The contact angle of a hydrophobic compound may be measured by numerous methods known to those skilled in the art and include, for example, the telescope-goniometer method, the Wilhelmy balance method, the capillary penetration method and the Washburn method. In embodiments of the invention, the solid substance comprising the hydrophobic compound has a contact angle greater than 90 degrees, but this angle is reduced to below 90 degrees after the substance is processed by the method of the invention. In preferred embodiments, the contact angle is reduced to below 80 degrees, or below 70 degrees, or below 60 degrees, or below 45 degrees, or below 30 degrees.

For example, particles of a solid substance comprising a target hydrophobic compound may have an average contact angle of about 110 degrees prior to being treated by the method of the invention, and this average contact angle may be reduced to about 65 degrees after treatment by the method of the invention. In another example, particles of a solid substance comprising a target hydrophobic compound may have an average contact angle of about 95 degrees prior to being treated by the method of the invention, and this average contact angle may be reduced to about 50 degrees after treatment by the method of the invention. In further examples, particles of a solid substance comprising a target hydrophobic compound may have an average contact angle above 120 degrees prior to being treated by the method of the invention, and this average contact angle may be reduced to less than 45 degrees after treatment by the method of the invention. In additional examples, particles of a solid substance comprising a target hydrophobic compound may have an average contact angle above 90 degrees prior to being treated by the method of the invention, and this average contact angle may be reduced to less than 75 degrees after treatment by the method of the invention. In yet another example, particles of a solid substance comprising a target hydrophobic compound may have an average contact angle above 150 degrees prior to being treated by the method of the invention, and this average contact angle may be reduced to less than 90 degrees after treatment by the method of the invention.

Whether the composition is liquid dispersible (or has improved dispersion properties) may be determined by the average particle size achieved when the liquid dispersible composition produced by the methods of the invention is mixed with water. Particle size may be measured using known methods. It would be understood that if the composition is not liquid dispersible, it would predominantly form aggregates or agglomerates with average particle sizes in excess of about 200 uM, when mixed with water. In one or more embodiments of the present invention, the liquid dispersible composition produces a population of particles when mixed with water, wherein greater than 50% of the population of particles are between 1 and 100 μm in diameter. Preferably, the particles are between 1 and 50 μm in diameter.

For example, 50%-80% of the population of particles may be less than about 100 pm in diameter, or at least 60% of the population of particles may be less than about 50 μm in diameter, or at least 70% of the population of particles may be less than about 50 μm in diameter, or at least 50% of the population of particles may be less than about 40 μm in diameter, or at least 50% of the population of particles may be less than about 30 μm in diameter.

The method of the present invention may improve the bioavailability of the hydrophobic compound. In general, the bioavailability of a compound is an indicator of the degree and rate a compound enters the circulatory system when introduced through ingestion, inhalation, injection, or skin contact. Determining the absolute bioavailability of a compound is done through pharmacokinetic studies, with which the skilled addressee would be familiar, and the results are generally provided in terms of plasma concentration of the compound. In embodiments of the invention, the bioavailability of the hydrophobic compound in the solid substance is increased after combining said solid substance comprising the hydrophobic compound with the dispersing agent whilst applying a shear force. Preferably, the bioavailability is increased by at least about 20%, 30%, 50%, 60%, 70%, 80%, 90%, 100%, 120%, 150% or 200% and above when compared to the bioavailability of the same solid substance comprising the hydrophobic compound that has not been treated by the method of the present invention.

In one embodiment of the invention, the solid substance comprising the hydrophobic compound has a contact angle greater than 90 degrees, but this angle is reduced to below 90 degrees after the substance is processed by the method of the invention, and the liquid dispersible composition produces a population of particles when mixed with water, wherein greater than 50% of the population of particles are between 1 and 100 μm in diameter, and the bioavailability of the hydrophobic compound in the solid substance is increased by at least 70% after combining said solid substance comprising the hydrophobic compound with the dispersing agent whilst applying a shear force.

In another embodiment, the solid substance comprising the hydrophobic compound has a contact angle greater than 90 degrees, but this angle is reduced to below 60 degrees after the substance is processed by the method of the invention, and the liquid dispersible composition produces a population of particles when mixed with water, wherein greater than 50% of the population of particles are between 1 and 50 μm in diameter, and the bioavailability of the hydrophobic compound in the solid substance is increased by at least 100% after combining said solid substance comprising the hydrophobic compound with the dispersing agent whilst applying a shear force.

In one embodiment of the invention, the liquid dispersible composition produces a population of particles when mixed with water, wherein at least 60% of the population of particles are between 1 and 40 μm in diameter, and the bioavailability of the hydrophobic compound in the solid substance is increased by at least 50% after combining said solid substance comprising the hydrophobic compound with the dispersing agent whilst applying a shear force.

In certain embodiments of the present invention, the dispersing agent comprises an amphiphilic molecule, comprising a hydrophobic portion and a hydrophilic portion.

Without wishing to be bound by theory, it is supposed that, when combining solid particles comprising the hydrophobic compound with the dispersing agent under a shear force, the hydrophobic portion of the amphiphilic molecules in the dispersing agent are forcibly embedded, connected or interfaced onto a non-wettable surface of a particle. Thus, the hydrophilic portion of the amphiphilic molecule may be exposed on the surface of the particles, thereby increasing the wettability and dispersibility of the solid substance when added to water. If embedded, connected or interfaced in sufficient quantities on a particle, the exposed hydrophilic portions of the amphiphilic molecules may effectively render the particle hydrophilic. In the event the hydrophilic portion of the dispersing agent is charged, repulsive forces between the particles may further enhance the liquid dispersibility of the particles.

In one or more embodiments of the present invention, the amphiphilic molecule is a surfactant. The surfactant may be any compound or composition suitable for producing mixtures of substances that would not ordinarily mix by, for example, lowering the surface tension of between a liquid and solid. In general, a surfactant consists of a hydrophilic head and a hydrophobic tail. The surfactant may be an ionic (cationic or anionic) surfactant, a zwitterionic surfactant, a phospholipid surfactant or a non-ionic surfactant, or combinations thereof.

The dispersing agent may comprise more than one surfactant, and the surfactants may be the same type or or a different type. For example, the dispersing agent may comprise two phospholipid surfactants and a non-ionic surfactant. In another example, the dispersing agent may comprise two non-ionic surfactants. In a further example, the dispersing agent may comprise a phospholipid surfactant, an anionic surfactant and a non-ionic surfactant.

The surfactant may be selected from the group consisting of hydrogenated castor oil, lecithin, macrogolglycerol hydroxystearate, oat oil polar lipids, phosphatidylcholine, poloxamers, polyoxyl 35 castor oil, polyoxyl 40 castor oil, polysorbate 20, polysorbate 60, polysorbate 80, polyglycerol polyricinoleate, D-alpha-tocopherol polyethylene glycol 1000 succinate (TPGS), glyceryl monooleate and polyglycerol esters of fatty acids. In preferred embodiments of the invention, the dispersing agent comprises a non-ionic surfactant and/or a phospholipid surfactant. The dispersing agent may comprise one or more surfactants, wherein the total amount of surfactant in the dispersing agent is 5% (w/w)-99% (w/w). Preferably, the total amount of surfactant in the dispersing agent is 10% (w/w)-90% (w/w). In other embodiments, the total amount of surfactant in the dispersing agent is 50% (w/w)-75% (w/w), or 10% (w/w)-25% (w/w), 50% (w/w)-99% (w/w), 20% (w/w)-75% (w/w), 5% (w/w)-15% (w/w).

For example, the dispersing agent may comprise about 0.5% (w/w)-10% (w/w) of one or more phospholipid surfactants and 60% (w/w)-99% (w/w) of one or more non-ionic surfactants, or the dispersing agent may comprise a total of at least about 2.5% (w/w)-10% (w/w) phospholipid surfactants and a total of at least 70% (w/w)-99% (w/w) of non-ionic surfactants. In other examples, the dispersing agent may only comprise one surfactant at about 50% (w/w)-70% (w/w), or dispersing agent may comprise about 0.2% (w/w)-10% (w/w) of one surfactant such as lecithin and 60% (w/w)-99% (w/w) of a different surfactant, such as hydrogenated castor oil or a derivative or precursor thereof.

In other examples, the dispersing agent may comprise 60% (w/w)-99% (w/w) hydrogenated castor oil, 0.2% (w/w/)-2.5% (w/w) lecithin or oat oil, and/or 0.5% (w/w)-5% (w/w) glyceryl monooleate, or the dispersing agent may comprise 5% (w/w)-50% (w/w) phospholipid surfactant, and 0.5% (w/w)-5% (w/w) of a different surfactant. In a further example, the dispersing agent comprises two or more surfactants selected from the group consisting of hydrogenated castor oil, lecithin, macrogolglycerol hydroxystearate, oat oil, polar lipids, phosphatidylcholine, poloxamers, polyoxyl 35 castor oil, polyoxyl 40 castor oil, polysorbate 20, polysorbate 60, polysorbate 80, polyglycerol polyricinoleate, D-alpha-tocopherol polyethylene glycol 1000 succinate (TPGS), glyceryl monooleate and polyglycerol esters of fatty acids, wherein each of the surfactants are present at a concentration of 0.5% (w/w)-70% (w/w).

In one or more embodiments of the invention, the dispersing agent further comprises a carrier oil selected from the group consisting of medium chain triglycerides, long chain triglycerides, caprylic and/or capric triglycerides, coconut oil, corn oil, cottonseed oil, olive oil, sesame oil, soybean oil, peanut oil, castor oil and oleic acid. The dispersing agent may comprise one or more carrier oils, wherein the total amount of carrier oil in the dispersing agent is 1% (w/w)-50% (w/w). Preferably, the total amount of carrier oil in the dispersing agent is 5% (w/w)-30% (w/w). More preferably, the total amount of carrier oil in the dispersing agent is 10% (w/w)-25% (w/w).

In one or more embodiments of the invention, the dispersing agent comprises two or more carriers oils selected from the group consisting of medium chain triglycerides, long chain triglycerides, caprylic and/or capric triglycerides, coconut oil, corn oil, cottonseed oil, olive oil, sesame oil, soybean oil, peanut oil, castor oil and oleic acid, wherein each of the carrier oils is present at a concentration of 0.5% (w/w)-10% (w/w), or 1.5% (w/w)-20% (w/w). In further embodiments of the invention, the dispersing agent comprises medium chain triglycerides, olive oil and/or coconut oil.

In other embodiments of the invention, the dispersing agent further comprises a solvent selected from the group consisting of citrus oil, ethanol, ethyl oleate, glycerine, glyceryl mono-oleate, limonene, polyethylene glycol 300, polyethylene glycol 400, polyethylene glycol 600 and propylene glycol. The dispersing agent may comprise one or more solvents, wherein the total amount of carrier oil is in the solvent is 1% (w/w)-30% (w/w). More preferably, the total amount of carrier oil in the dispersing agent is 1% (w/w)-10% (w/w). In preferred embodiments, the dispersing agent comprises 0.5%-15% (w/w) citrus oil, and/or 0.5%-25% (w/w) a poly ethylene glycol.

In one or more embodiments of the present invention, the dispersing agent comprises an amphiphilic molecule and a carrier oil. In other embodiments, the dispersing agent comprises an amphiphilic molecule and solvent. In preferred embodiments, the dispersing agent comprises an amphiphilic molecule, a solvent and a carrier oil. In preferred embodiments, the dispersing agent comprises 10% (w/w)-99% (w/w) total surfactant, 1% (w/w)-30% (w/w) total solvent and 5% (w/w)-30% (w/w) total carrier oil. In preferred embodiments, the dispersing agent comprises 50% (w/w)-75% (w/w) total surfactant, 2.5% (w/w)-15% (w/w) total solvent and 1% (w/w)-10% (w/w) total carrier oil.

For example, the dispersing agent may comprise 60% (w/w)-75% (w/w) non-ionic surfactant, 0.2% (w/w)-10% (w/w) phospholipid surfactant, 2.5% (w/w)-15% (w/w) citrus oil, and 10% (w/w)-25% (w/w) total carrier oil.

The dispersing agent may further comprise a preservative, such as an anti-microbial or an anti-oxidant. In an embodiment of the present invention, the preservative is an anti-oxidant is selected from the group consisting of ascorbyl palmitate, d alpha-tocopherol, dl-alpha-tocopherol, d-alpha-Tocopheryl acetate, dl-alpha-Tocopheryl acetate, d-alpha-Tocopheryl acid succinate, dl alpha-Tocopheryl acid succinate, Vitamin E and derivatives thereof, olive polyphenols and algal polyphenols. In preferred embodiments of the invention, the dispersing agent may comprise a preservative at a concentration of 0.1% -5% (w/w).

The dispersing agent and the solid substance comprising the hydrophobic compound may be combined at any ratio that will facilitate the production of the liquid dispersible composition comprising the hydrophobic compound. In embodiments of the present invention, the ratio of the solid substance comprising the hydrophobic compound and the dispersing agent is from about 100:1 to about 1:1. Preferably, the ratio of the solid substance comprising the hydrophobic compound and the dispersing agent is from about 20:1 to about 5:1. In other preferred embodiments, the ratio of the solid substance comprising the hydrophobic compound and the dispersing agent is about 10:1, about 9:1 or about 8:1.

In one or more embodiments of the present invention, the substance comprising the hydrophobic compound is combined with the dispersing agent in the presence of an anti-caking agent. Anti-caking agents function by the absorption of excess moisture. By definition, anti-caking agents are anhydrous compounds that are added in small amounts to dry products to prevent the particles caking together and ensure the product remains dry and free-flowing. Non-limiting examples of anticaking agents include the stearates of calcium and magnesium, silica and various silicates, talc, as well as flour and starch. In preferred embodiments of the invention, the anti-caking agent is a silica-based agent.

The selection and concentration of components in the dispersing agent, as well as the ratio at which the dispersing agent and solid substance comprising the hydrophobic substance are combined, will depend on numerous factors such as the nature of the solid substance, the hydrophobicity of the hydrophobic compound and the desired end use of the liquid dispersible composition.

A shear force is created when forces are applied to a mixture in one direction, in conjunction with forces in the opposite direction, within the same parallel plane. In the methods of the present invention, the shear force is required to embed, connect or interface the dispersing agent onto the non-wettable surfaces of the particles of the solid substance.

The shear force used during the method of the invention may also contribute to a reduction in the particle size of the solid substance, as well as reducing the angularity of the particles of the solid substance, both of which may enhance dispersibility by reducing the potential for aggregation and agglomeration of the resulting composition in water.

In one or more embodiments of the present invention, shear force is created by high shear mixing of the solid substance with the dispersing agent. The skilled addressee would understand that high shear mixing can be achieved by numerous methods, including, but not limited to, milling (such as ball milling, pin milling, jet milling and colloidal milling, or grinding with mortar and pestle), rotor-stator mixing, blending, chopping, high-pressure homogenisation and combinations thereof.

The hydrophobic compound may be any compound that has a commercial application wherein it is preferable that the hydrophobic compound, or a substance comprising the hydrophobic compound, is at least partially liquid dispersible The hydrophobic compounds of the present invention may be obtained from commercially available sources and/or prepared, isolated or derived for source material. The hydrophobic compound may be a synthetic compound, a natural compound or a semi-synthetic compound. For example, the compound may be chemically synthesised, isolated from an animal or plant source, or may be in the form of an extract from an animal or plant source, or combinations thereof.

Extracts from plant and animal sources may be prepared by methods known to those skilled in the art and may include processes such as water extractions, chromatographic extractions, solvent extractions, lipid-phase and solid phase extractions, precipitations steps, drying steps, and clarification and purification steps.

In one or more embodiments of the present invention, the hydrophobic compound is a protein. The protein may be derived from an animal milk, such as whey protein or casein. The protein may be a serum albumin or a membrane protein or any protein with nutritional benefits.

In one or more embodiments of the present invention, the hydrophobic compound is a fat. The fat may have nutritional value or be therapeutically beneficial. Preferably, the fat is a fatty acid ethanolamide FAEs). In embodiments of the invention, the hydrophobic compound is oleoylethanolamide (OEA), palmitoylethanolamide (PEA), arachidonoylethanolamide (anandamide), and/or combinations thereof. The FAE are known multifunctional lipid mediators, and may be isolated from a plant or animal source.

In one or more embodiments of the present invention, the hydrophobic compound is fat-soluble benzoquinone. Preferably, the compound is a ubiquinone. Ubiquinone (or ubiquinol) has been used as an antioxidant and antiaging health supplement and to alleviate conditions linked to mitochondrial dysfunction.

In one or more embodiments of the present invention, the hydrophobic compound is a phytochemical, preferably a polyphenol, or a derivative thereof. The polyphenols are a large class of plant metabolites implicated for the treatment and prevention of numerous diseases and disorders due to their anti-oxidant effect. Sub-classes on the polyphenols are the hydrobenzoic acids, hydroxycinnamic acids, flavonoids, stilbenes and lignans, and they are found largely in fruits and vegetables.

In certain embodiments of the present invention, the hydrophobic compound is a hydroxycinnamic acid, a flavonoid or a stilbene.

In one or more embodiments of the invention, the hydrophobic compound is a hydroxycinnamic acid, or derivative thereof, selected form the group consisting of coumaric acid, caffeic acid, ferulic acid, sinapic acid or a curcuminoid. In a preferred embodiment of the invention, the hydroxycinnamic acid is a curcuminoid, or a derivative thereof. The most common curcuminoid is curcumin, which is a natural polyphenol derived most abundantly from turmeric (Curcuma longa). Curcumin has pleiotropic molecular effects and has been used in traditional medicine to treat various disorders, and in particular, inflammation.

In one or more embodiments of the present invention, the curcuminoid is selected from the group consisting of curcumin, demethoxycurcumin and bisdemethoxycurcumin.

In other embodiments of the present invention, the curcuminoid is in the form of an extract from a plant source, wherein the plant source is selected from the group consisting of turmeric, Devil's Claw, White Willow, ginger, grape seed extract, Giant knotweed and green tea.

In further embodiments of the invention, the hydrophobic compound is a flavonoid, or derivative thereof, selected from the group consisting of kaempferol, quercetin, myricetin or a catechin. In a preferred embodiment of the invention, the flavonoid is a quercetin, or a derivative thereof. The most abundant polyphenol in onion, quercetin has been shown to have cardiovascular benefits by inhibiting the expression of MMP1. Quercetin may also be found in apples and berries, and has been implicated as a potential therapeutic to treat cancer and proliferation disorders, chronic inflammation and various other oxidative manifestations.

In one or more embodiments of the present invention, the quercetin is in the form of an extract from a plant source, wherein the plant source is selected from the group consisting of onion, apple and cherry.

In certain embodiments of the invention, the hydrophobic compound is a stilbene, or derivative thereof. In a preferred embodiment of the invention, the stilbene is resveratrol, or a derivative thereof. Resveratrol is a wine polyphenol, as it is largely found in the skin of red grapes and has been shown to be a strong antioxidant, with potential benefits for the treatment of heart disease, cancer, diabetes and obesity.

In one or more embodiments of the present invention, the resveratrol is in the form of an extract from a plant source, wherein the plant source is selected from the group consisting of red grapes, Japanese knotweed, peanuts and blueberries.

In an embodiment of the present invention, the liquid dispersible composition comprises a polyphenol and a dispersing agent, wherein the dispersing agent comprises 10% (w/w)-99% (w/w) total surfactant, a carrier oil and a solvent, and wherein the solid substance comprising the polyphenol is combined with the dispersing agent with high shear mixing, and the ratio of said solid substance and dispersing agent is from about 20:1 to about 5:1.

In an embodiment of the present invention, the liquid dispersible composition comprises a FAE and a dispersing agent, wherein the dispersing agent comprises 10% (w/w)-99% (w/w) total surfactant, a carrier oil and a solvent, and wherein the solid substance comprising the FAE is combined with the dispersing agent with high shear mixing, and the ratio of said solid substance and dispersing agent is from about 20:1 to about 5:1.

In an embodiment of the present invention, the liquid dispersible composition comprises a protein and a dispersing agent, wherein the dispersing agent comprises 10% (w/w)-99% (w/w) total surfactant, a carrier oil and a solvent, and wherein the solid substance comprising the protein is combined with the dispersing agent with high shear mixing, and the ratio of said solid substance and dispersing agent is from about 20:1 to about 5:1.

In an embodiment of the present invention, the liquid dispersible composition comprises a benzoquinone and a dispersing agent, wherein the dispersing agent comprises a 10% (w/w)-99% (w/w) total surfactant, a carrier oil and a solvent, and wherein the solid substance comprising the benzoquinone is combined with the dispersing agent with high shear mixing, and the ratio of said solid substance and dispersing agent is from about 20:1 to about 5:1.

In a second aspect of the present invention, there is provided liquid dispersible compositions produced by the method of the invention.

Non-limiting uses for the liquid dispersible compositions produced by the method of the invention include dietary supplements, nutraceuticals and/or pharmaceuticals. A dietary supplement may be any product intended to supplement the diet and improve health and wellness. A nutraceutical may be any product derived from animal or plant sources with extra health benefits in addition to the basic nutritional value found in foods, and may be used to promote general well-being, control minor symptoms of disease and disorders and prevent malignant processes. In general, pharmaceuticals are synthetic or imitations of natural substances that the body needs to manufacture or utilize to maintain health and fight disease and disorders. The skilled addressee would also appreciate that dietary supplements, nutraceuticals and pharmaceutical are distinguishable by the regulatory thresholds they must meet.

In a further aspect of the present invention, there is provided the use of a liquid dispersible composition of a hydrophobic compound that is a protein in the manufacture of a dietary supplement. The supplement may be in tablet form or provided as a powder to be dispersed in a liquid and consumed as a drink.

Liquid dispersible compositions comprising hydrophobic compounds with therapeutic benefits prepared using the methods of the invention may be used as nutraceuticals and/or pharmaceuticals.

In a further aspect of the present invention, there is provided the use of a liquid dispersible composition comprising a fatty acid ethanolamine (FAE) in the manufacture of a medicament for the treatment or prevention of a disease or disorder selected from the group consisting of obesity, pain, inflammation and immune disorders. In a preferred embodiment, the FAE is oleoylethanolamide and the medicament is for the treatment or prevention of obesity. In a further preferred embodiment, the FAE is palmitoylethanolamide and the medicament is for the treatment or prevention of pain and inflammation. agent such as alginic acid, Primogel, or corn starch; a lubricant such as magnesium stearate; a glidant such as colloidal silicon dioxide; a sweetening agent such as sucrose or saccharin; or a flavouring agent.

Definitions

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The term "treatment", and the like, in the context of the present specification includes the alleviation of the symptoms related to a disease or disorder. The treatment may cure the disease or disorder. Hence, in the context of this invention the word "treatment" or derivations thereof when used in relation to a therapeutic application includes all aspects of a therapy, such as the alleviation of pain associated with the disease or disorder, alleviation of the severity of the disease or disorder, improvement in one or more symptoms of the disease or disorder, improvement in the overall well-being of the subject being treated. Use of the word "treatment" or derivatives thereof will be understood to mean that the subject being "treated" may experience any one or more of the aforementioned benefits.

The term "prevention", and the like, in the context of the present specification refers to the prevention of the recurrence of all or some of the symptoms associated with a disease or disorder, as well as the prevention of the spread of the disease or disorder.

In the context of this specification the term "about" will be understood as indicating the usual tolerances that a skilled addressee would associate with the given value.

In the context of this specification, where a range is stated for a parameter it will be understood that the parameter includes all values within the stated range, inclusive of the stated endpoints of the range.

In the context of the present invention, the term "subject" refers to an animal, preferably a mammal, most preferably a human, who has experienced and/or exhibited at least one symptom associated with a referred to disease or disorder. Further, as used herein, a "subject in need thereof" may additionally be a subject who has not exhibited any symptoms of a particular disease or disorder, but who has been deemed by, for example, a physician, clinician or other medical professional, a naturopath or other practitioner to be at risk of developing said disease or disorder. For example, the subject may be deemed to be at risk of developing a particular disease or disorder (and therefore in need of prevention or preventive treatment) as a consequence of the subject's medical history, including, but not limited to, family history, pre-disposition, co-existing/contributory injuries or disorders and genetic testing.

Throughout this specification, unless specifically stated otherwise or the context requires otherwise, reference to a single step, composition of matter, group of steps or group of compositions of matter shall be taken to encompass one and a plurality (i.e. one or more) of those steps, compositions of matter, groups of steps or group of compositions of matter.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations or any two or more of said steps or features.

The present invention is not to be limited in scope by the specific embodiments described herein, which are intended for the purpose of exemplification only. Functionally-equivalent products, compositions and methods are clearly within the scope of the invention, as described herein.

BRIEF DESCRIPTION OF DRAWINGS

Embodiments of the invention will now be described, by way of example only, with reference to the accompanying drawings in which.

DETAILED DESCRIPTION OF THE PREFERRED EMBODIMENTS

EXAMPLE 1

Liquid Dispersible Compositions Comprising Curcumin

Preliminary Study

Batch# CUR BT20170206_01 was prepared with 9 g of curcumin longa extract and 0.874 g of a dispersing agent prepared with 70% (w/w) Etocas 35, 20% (w/w) medium chain triglycerides, 4.5% (w/w) lime oil, 1.5% (w/w) olive oil, 2.5% (w/w) glyceryl mono-oleate, 0.5% (w/w/) vitamin E acetate, 0.5% (w/w) lecithin and 0.5% (w/w) oat oil, in the presence of 0.106 g of Silica colloidal anhydrous. The extract, dispersing agent and silica were combined with high shear mixing by shaking vigorously in a plastic bottle with metal ball bearings.

Figure 4:
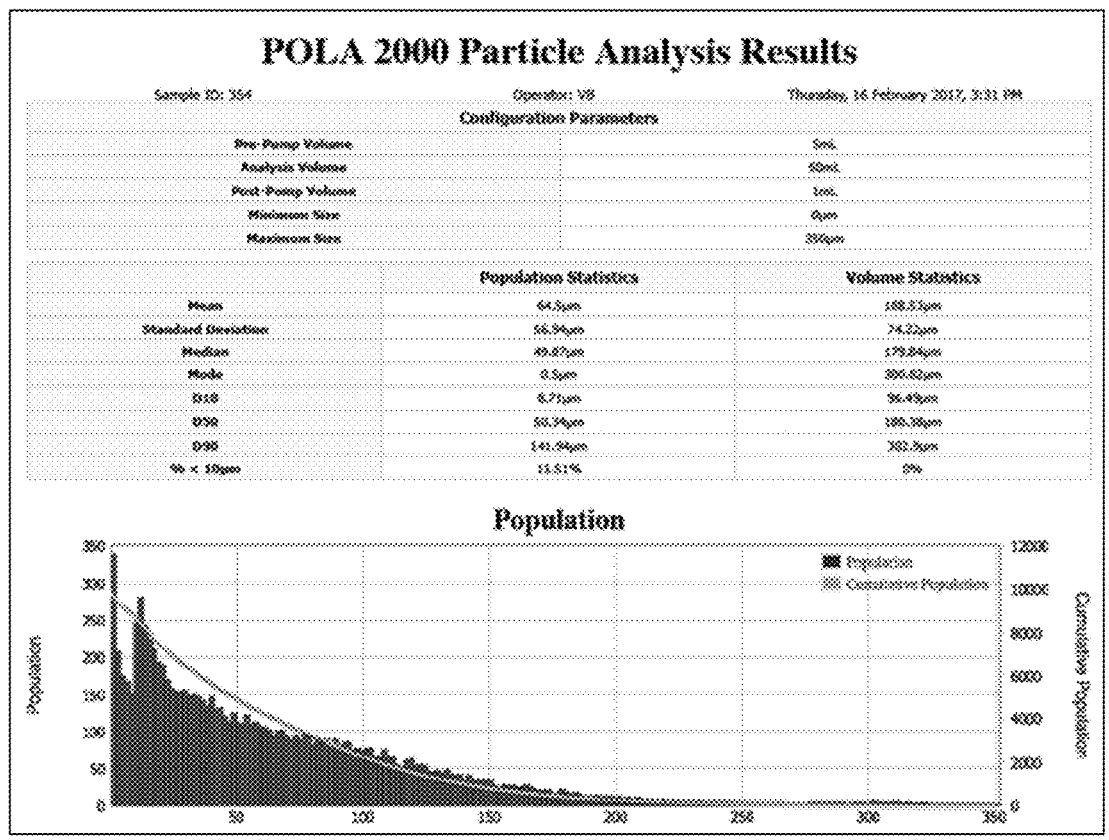
FIG. 4: Particle analysis results for Batch# CUR BT20170206_01.

A sample of the resulting composition (0.5 g mixed with 250 ml of water) was assayed for particle size by Particle & Surface Sciences Pty Ltd (Gosford, AUST). The mean particles size was 64.5 µM (see FIG. 4).

Medium Scale Preparations

Batch# CurcuminCWD BT20170303_01 was prepared with 902 g of curcuma longa extract and 90 g of a dispersing agent prepared with 70% (w/w) Etocas 35, 20% (w/w) medium chain triglycerides, 4.5% (w/w) lime oil, 1.5% (w/w) olive oil, 2.5% (w/w) glycerol mono-oleate, 0.5% (w/w/) vitamin E acetate, 0.5% (w/w) lecithin and 0.5% (w/w) oat oil, in the presence 10 g of Silica colloidal anhydrous. The extract, dispersing agent and silica were combined with high shear mixing over two hours using continuously rotating drum mixer in a 5 L plastic bottle with 5×20mM metal ball bearings.

Figure 5:
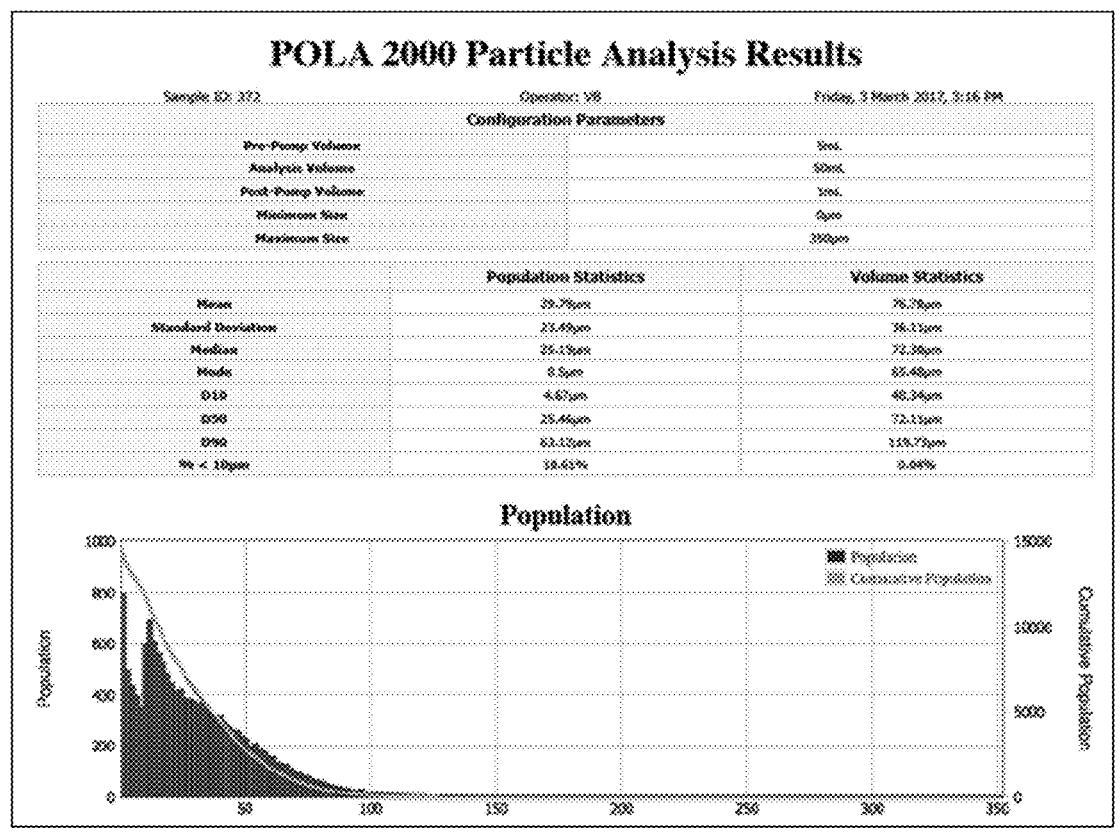
FIG. 5: Particle analysis results for Batch# CurcuminCWD BT20170303_01A.
Figure 6:
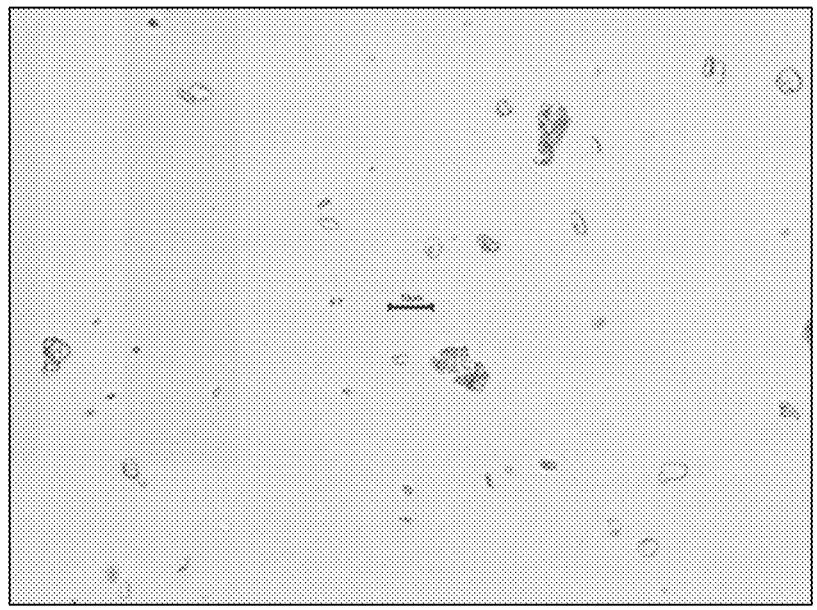
FIG. 6: Sample of Batch# CurcuminCWD BT20170303_01A dispersed in water and viewed microscopically under 40× magnification.

A sample of the resulting composition was assayed for particle size by Particle & Surface Sciences Pty Ltd (Gosford, AUST) (FIG. 5), and viewed microscopically under 40× magnification (FIG. 6). The mean particles size was 29.79 µM.

Batch# CurcuminCWD BT20170315_02 was prepared with 237 g of curcuma longa extract and 23 g of a dispersing agent prepared with 70% (w/w) Etocas 35, 20% (w/w) medium chain tryglycerides, 4.5% (w/w) lime oil, 1.5% (w/w) olive oil, 2.5% (w/w) glycerol mono-oleate, 0.5% (w/w/) vitamin E acetate, 0.5% (w/w) lecithin and 0.5% (w/w) oat oil, and 2.67 g of Silica colloidal anhydrous. The extract, dispersing agent and silica were combined with high shear mixing over two hours using a continuously rotating drum mixer in a plastic bottle with 5×20mM metal ball bearings.

Figure 7:
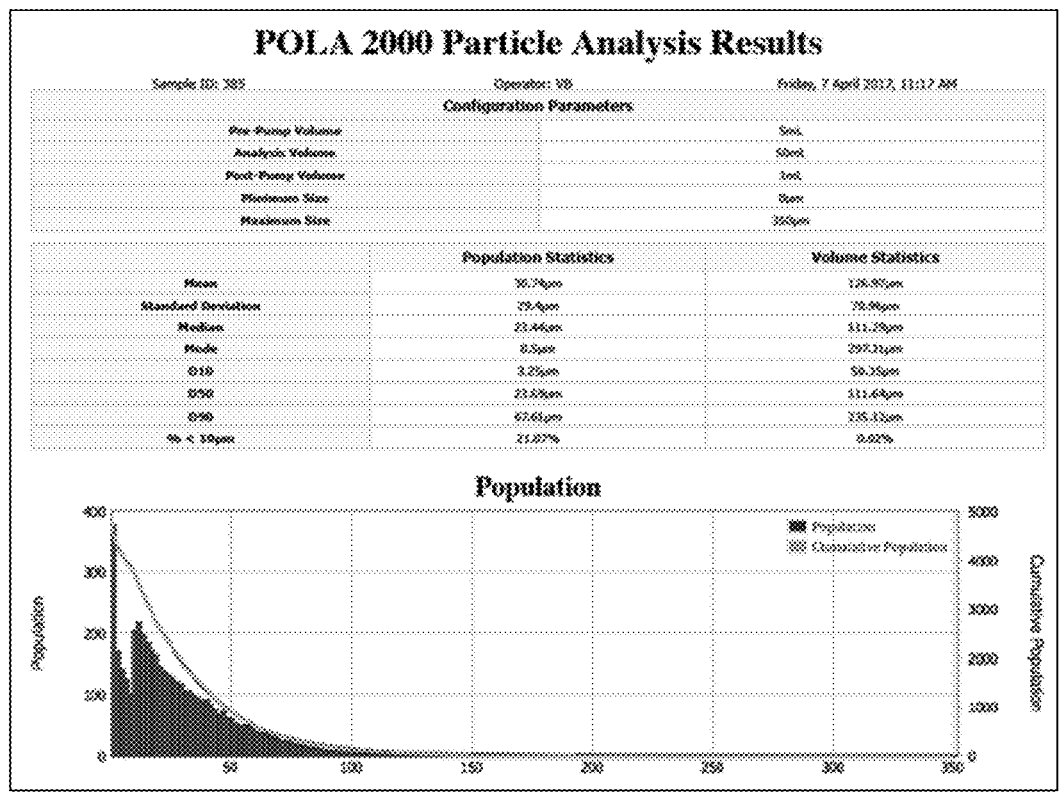
FIG. 7: Particle analysis results for Batch# CurcuminCWD B120170315_02.

A sample of the resulting composition was assayed for particle size by Particle & Surface Sciences Pty Ltd (Gosford, AUST) (FIG. 7). The mean particles size was 30.74 µM.

Batch# NaturexCurcuminCWD BT20170529_01 was prepared with 575 g of curcuma longa extract and 30 g of a dispersing agent prepared with 70% (w/w) Etocas 35, 20% (w/w) medium chain triglycerides, 4.5% (w/w) lime oil, 1.5% (w/w) olive oil, 2.5% (w/w) glycerol mono-oleate, 0.5% (w/w/) vitamin E acetate, 0.5% (w/w) lecithin and 0.5% (w/w) oat oil. The extract and dispersing agent were combined with high shear mixing over two hours using a continuously rotating drum mixer in a plastic bottle with 8×20 mM metal ball bearings.

A sample of the resulting composition was assayed for particle size by Particle & Surface Sciences Pty Ltd (Gosford, AUST). The mean particles size was 30.03 µM.

Large Scale Preparation

Batch#MT20170428_03CurcuminCWD90 was prepared with 16.08 kg of curcuma longa extract and 1.61 kg of a dispersing agent prepared with 70% (w/w) Etocas 35, 20% (w/w) medium chain triglycerides, 4.5% (w/w) lime oil, 1.5% (w/w) olive oil, 2.5% (w/w) glycerol mono-oleate, 0.5% (w/w/) vitamin E acetate, 0.5% (w/w) lecithin and 0.5% (w/w) oat oil, and 0.18 kg of Silica colloidal anhydrous. The extract and dispersing agent were combined with high shear mixing in a rotor-stator mixer (High Shear Mixer-LHS300, SAR Labortecnic; 100-150 rpm for impeller and 1000-2000 rpm for cutting blades, with 5 min bursts for 35 min total). The silica was only added after an initial mixing step with 100 rpm impeller speed and 1000 rpm cutting blade speed.

Figure 8:
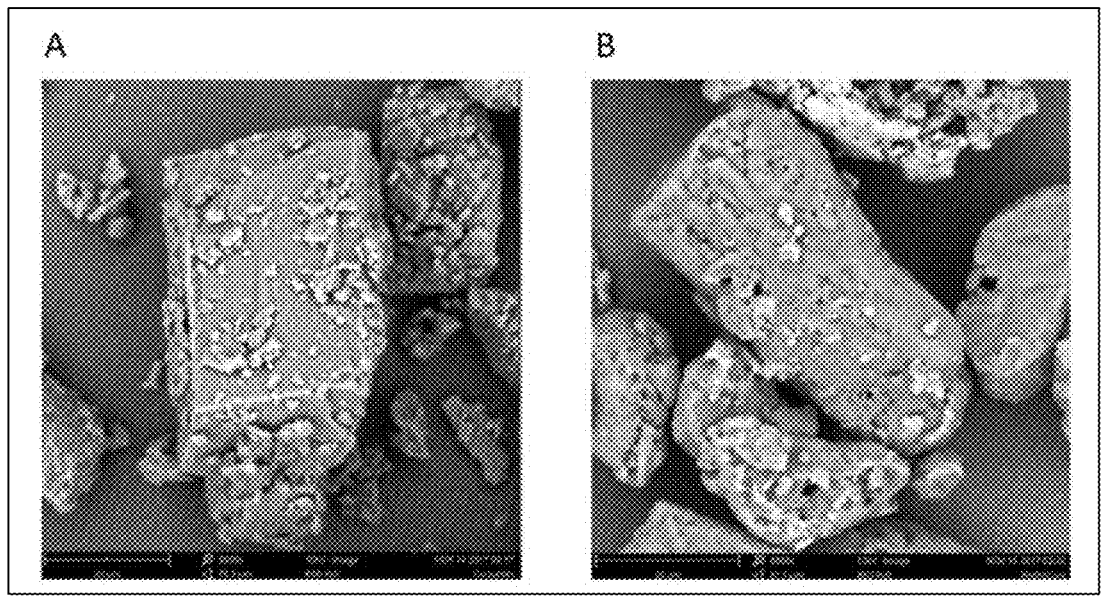
FIG. 8: SEM image of particles of Batch#MT20170428_03CurcuminCWD90 (B) compared to particles of curcumin alone.

A sample of the resulting composition was assayed for particle size by Particle & Surface Sciences Pty Ltd (Gosford, AUST). The mean particles size was 23.05 µM. A part of the composition was analysed by SEM (FIG. 8), which showed that the particles have smoother edges (B) than particles of curcumin that had not been combined with the dispersing agent under high shear (A).

Figure 9:
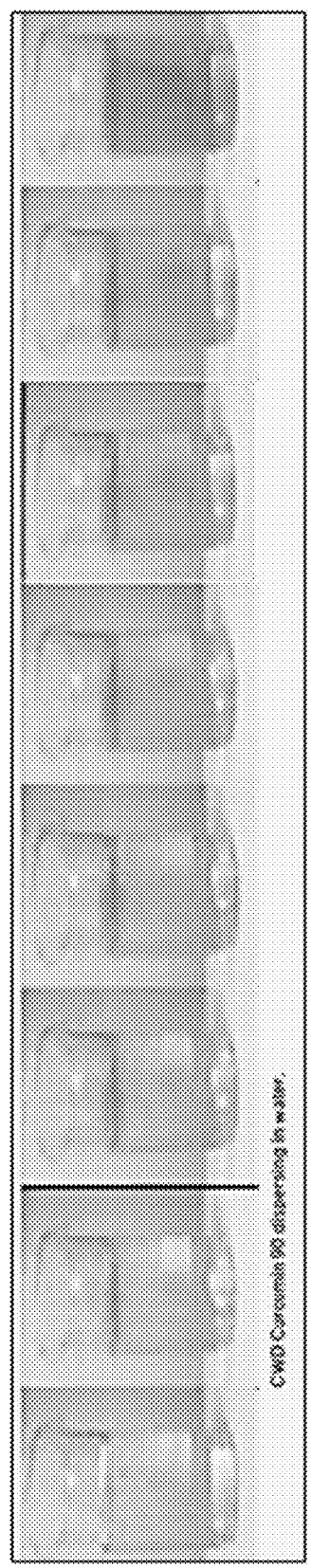
FIG. 9: Time lapse of passive dispersion of sample of Batch#MT20170428_03 CurcuminCWD90 in water.
Figure 10:
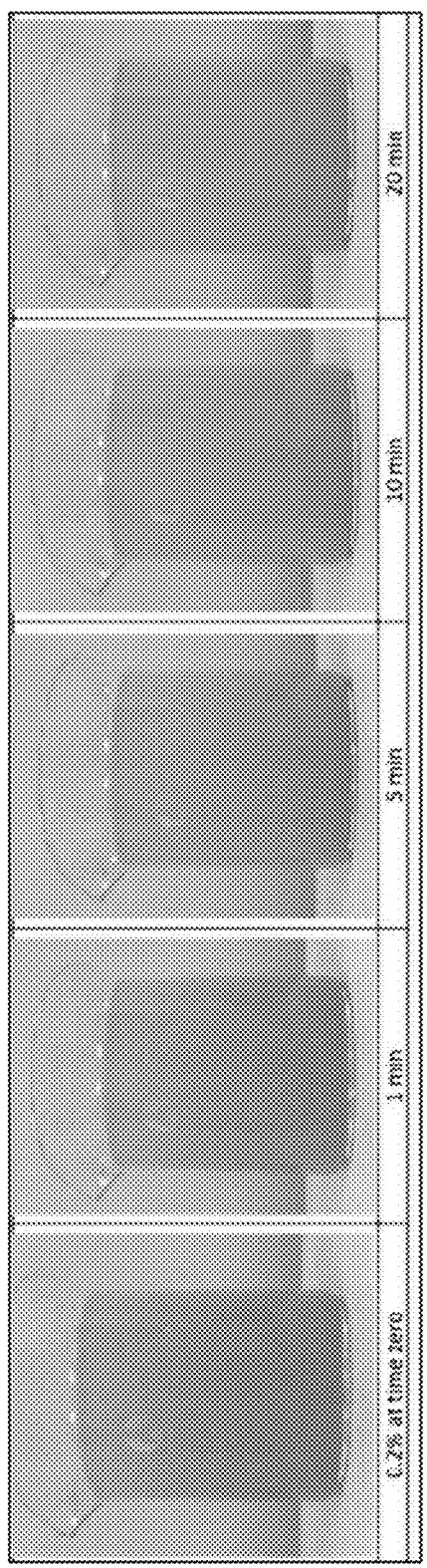
FIG. 10: Time lapse of dispersed sample of Batch#MT20170428_03 CurcuminCWD90 in water.

A sample was added to water to assay the dispersion of the composition. FIG. 9 shows that, over time, the curcumin passively disperses in water without mixing. A sample of the composition was added to water and mixed and allowed to stand. FIG. 10 shows that the curcumin remains dispersed after 20 minutes.

EXAMPLE 2

Enhance Bioavailability of Liquid Dispersible Composition Comprising Curcumin

Low bioavailability of any pharmaceutical agent within the body is due to; 1) poor gastrointestinal absorption, 2) high rates of metabolism, 3) inactivity of metabolic products and, 4) rapid elimination and clearance. Owing to its tautomeric structure, high molecular weight and aromatic groups, curcumin is extremely hydrophobic and therefore inadequately absorbed through the gastrointestinal epithelium. The study aimed to compare the pharmacokinetics of a single dose of commercially available curcumin with a curcumin-LipiSperse delivery complex. The curcumin-LipiSperse delivery complex is Batch#MT20170428_03 CurcuminCWD90 from Example 1.

Study Parameters

A single equivalent dose, randomised, double blinded parallel design with crossover was used to evaluate the pharmacokinetics of a commercially availability curcumin product, with or without the curcumin-LipiSperse delivery complex. 18 healthy volunteers (9 females, 9 males) were recruited to take part in this study. Following recruitment, participants were allocated into one of the two treatment groups, and all subjects and investigators were blinded to the allocations until analysis of all plasma samples had been completed.

The study arms were as follows: 1) Curcumin CWD 90 with LipiSperse (Pharmako Biotechnologies, New South Wales; Batch#MT20170428_03 CurcuminCWD90 from Example 1) hard shell capsule (2×440 mg) containing 90% Curcuma longa extract and 10% LipiSperse and 2) Standard curcumin capsule (4×200 mg) containing 100% Curcuma longa extract with 95% curcuminoids. Curcuma longa extract contains 95% curcuminoids. Both products therefore provided a total dose of 750 mg of curcuminoids (80% curcumin, 17% DMC and 3% BDMC by weight). Participants were required to complete an overnight fast (12-hours) prior to the day of testing. Curcumin pharmacokinetics were determined from blood samples taken prior to dosing (t=0), followed by intervals of 1,1.5, 2, 2.5, 3, 3.5, 4, 4.5, 5, 5.5, 6 and 24 hours post supplementation.

Sample Preparation

Plasma samples were extracted in accordance with standard methods. Briefly, plasma samples were removed from storage at −80° and allowed to thaw. Once thawed, 200 µL of sample or standard (1 µg/mL, 0.1 µg/mL, 0.01 µg/mL) was added to a microfuge tube, along with 50 µL of IS in methanol and 20 µL of 3M HCl (to liberate free curcumin). This solution was briefly vortex mixed before being spiked with 100 µL of a solution containing 5 U/mL of type H-1

β-glucuronidase/sulfatase (G0751) from Helix pomatia (Sigma-Aldrich, Castle Hill, NSW) in 0.1 M phosphate buffer (pH 6.86). For enzymatic hydrolysation of the conjugates of curcumin, the resultant mixture was vortex mixed for 30 seconds and incubated at 37 °C. for 1 h. During incubation, samples were constantly mixed. Following incubation, 1 mL of an extraction solution (95% ethyl acetate, 5% methanol) was added before samples were vortex mixed and sonicated for 15 minutes. The resulting solution was centrifuged at 13,000 g for 10 minutes and the upper organic layer extracted to glass test tube and dried under nitrogen at 37 degrees. Samples were reconstituted with 100 μl of methanol and transferred to a HPLC limited volume insert (200 μL capacity).

Analysis

Chromatographic separation was carried out on an Agilent 1260 Infinity HPLC system using a Kinetex 5 μm C18, 250×4.6 mm with an AQ C18 4×3 mm SecurityGuard cartridge. The column temperature was maintained at 30° C. and the analytes were quantified with an Agilent 6460 triple quad mass spectrometer with transitions as follows: Curcumin 369.2→285.2; demethoxycurcumin 338.9→255.0; bisdemethoxycurcumin 309.1→255.0.

Data were analysed using GraphPad Prism 7.0 (GraphPad Software Inc., California). Results are given as the mean±SD unless otherwise stated.

Results

No significant differences were reported in baseline curcumin, DMC or BDMC between either group both in the parallel and crossover trial (p<0.05). Baseline plasma concentrations for all curcuminoids were undetectable via HPCL. In the crossover trial, Cmax significantly increased in the CWD90 with LipiSperse group as demonstrated by an 807 ng/mL increase in total plasma curcuminoids from baseline values (p<0.05) (Se Tables 1 and 2, below). Whilst the standard curcumin treatment also delivered a significant increase in total plasma curcuminoids from baseline (p<0.05), the reported Cmax for this group was significantly less than that of CWD90 with LipiSperse (p<0.05). Similar findings were seen in the parallel phase of the trial. Both treatment groups delivered significant increases in total plasma curcuminoids from baseline values (p<0.05), however Cmax values for the CWD90 with LipiSperse group were significantly greater than the standard curcumin group (p<0.05).

Figure 11:
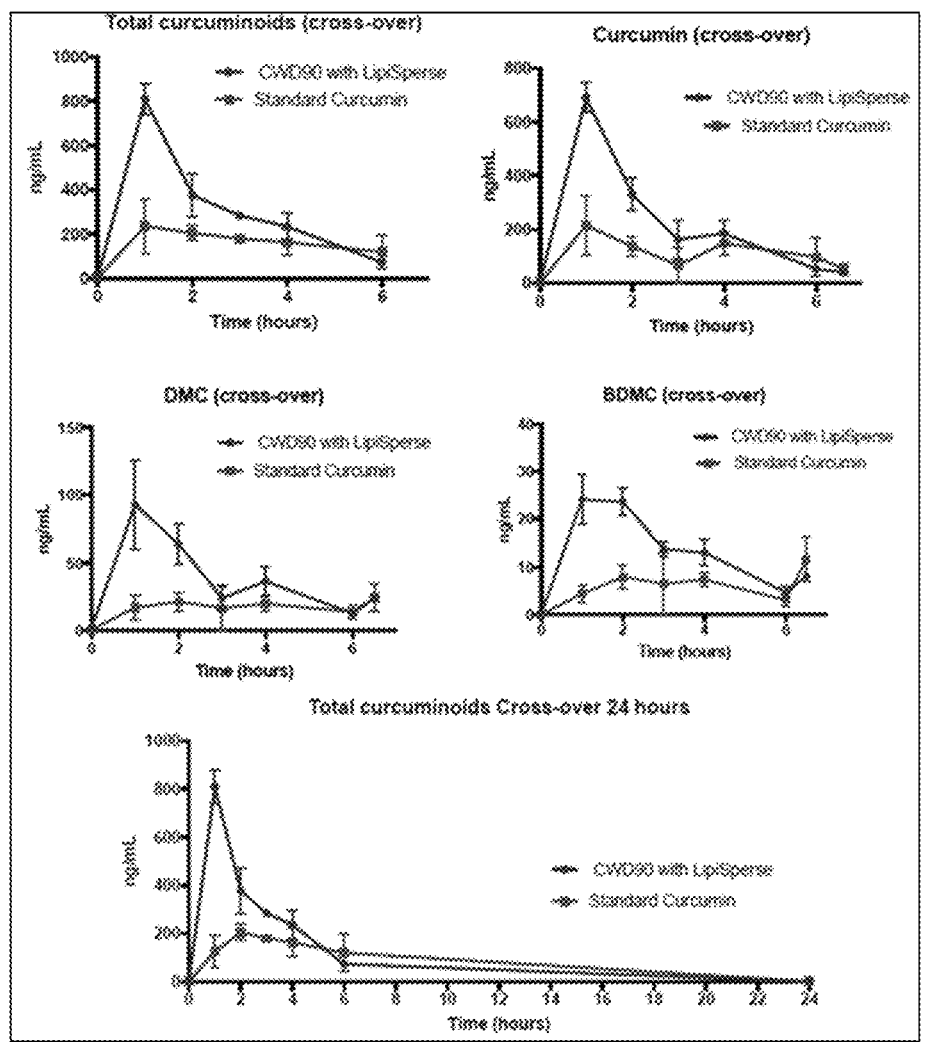
FIG. 11: Plasma concentration time curves during the cross-over trial for total curcuminoids (top left), curcumin (top right), DMC (bottom left), and BDMC (bottom right) after a single 750 mg dose of the two different curcumin preparations (Standard curcumin and Batch#MT20170428_03 CurcuminCWD90). Concentrations are expressed in ng/mL. n=5 per group.
Figure 12:
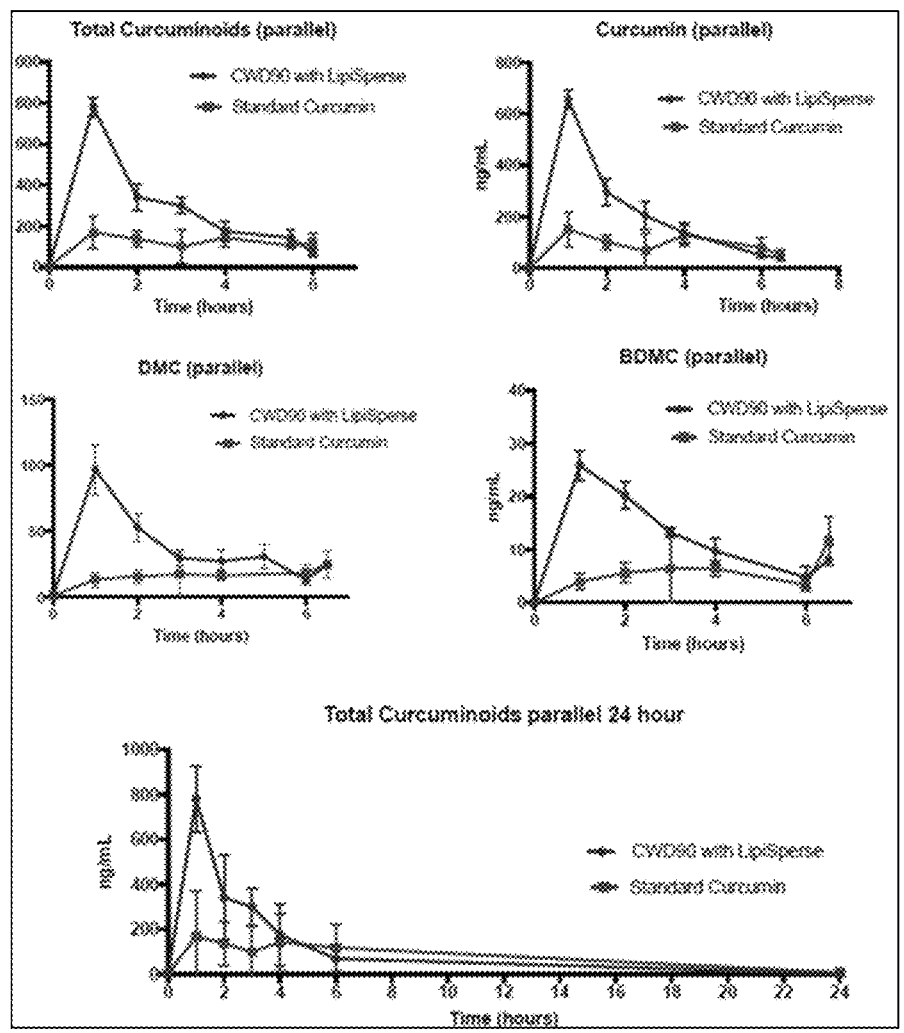
FIG. 12: Plasma concentration time curves during the parallel trial for total curcuminoids (top left), curcumin (top right), DMC (bottom left), and BDMC (bottom right) after a single 750 mg dose of the two different curcumin preparations. Concentrations are expressed in ng/mL. n=8 (CWD90 with LipiSperse, Batch#MT20170428_03 CurcuminCWD90), n =9 (standard curcumin).

Temporal data for of all curcuminoids measured during the crossover and parallel phase of the trial are reported in FIGS. 11 and 12, respectively. For both formulations across each phase of the trial, total plasma curcuminoid concentrations peaked at one hour following ingestion. All data returned to zero at the 24-hour mark.

TABLE 1

Cross-over pharmacokinetic parameters for curcumin. DMC, BDMC, and total curcuminoids after a single 750 mg dose of the two different curcumin preparations. Values for $C_{max}$ are reported in ng/mL. $T_{max}$ is reported in hours. Total $AUC_{(0-6\ H)}$ is reported as ng/mL. Relative $AUC_{(0-6\ H)}$ is reported as ng/mL/hour. Values reported as mean ± SD.

|  | GROUP 1 CWD90 with Lipisperse n = 5 | | | | GROUP 2 Standard Curcumin n = 5 | | | |
| --- | --- | --- | --- | --- | --- | --- | --- | --- |
|  | Curcmin | DMC | BDMC | Total | Curcumin | DMC | BDMC | Total |
| $C_{MAX}$ | 691 ± 124 | 9 ± 273 | 24 ± 11 | 807 ± 155 | 215 ± 224 | 22 ± 15 | 8 ± 5 | 318 ± 154 |
| $T_{MAX}$ | 1 | 1 | 1 | 1 | 1 | 2 | 2 | 1 |
| Total $AUC_{(0-6\ H)}$ | 1549 ± 206 | 260 ± 51 | 89 ± 13 | 1898 ± 270 | 787 ± 219 | 110 ± 31 | 36 ± 10 | 933 ± 260 |
| Relative $AUC_{(0-6\ H)}$ | 258 ± 34 | 438 ± 8 | 15 ± 2 | 316 ± 45 | 131 ± 36 | 18 ± 5 | 6 ± 2 | 155 ± 43 |
| Total $AUC_{(0-24\ H)}$ | 1998 ± 288 | 366 ± 77 | 128 ± 27 | 2492 ± 392 | 1621 ± 113 | 226 ± 87 | 60 ± 21 | 1907 ± 221 |
| Relative $AUC_{(0-24\ H)}$ | 83 ± 12 | 15 ± 3 | 5 ± 1 | 104 ± 16 | 68 ± 5 | 9 ± 4 | 3 ± 1 | 79 ± 9 |

|  | GROUP 1 Cwd90 with Lipisperse n = 8 | | | | GROUP 2 Standard Curcumin n = 9 | | | |
| --- | --- | --- | --- | --- | --- | --- | --- | --- |
|  | Curcmin | DMC | BDMC | Total | Curcumin | DMC | BDMC | Total |
| $C_{MAX}$ | 658 ± 116 | 97 ± 59 | 26 ± 8 | 781 ± 147 | 151 ± 184 | 17 ± 15 | 7 ± 9 | 267 ± 153 |
| $T_{MAX}$ | 1 | 1 | 1 | 1 | 1 | 3 | 2 | 1 |
| Total $AUC_{(0-6\ H)}$ | 1438 ± 206 | 253 ± 52 | 82 ± 13 | 1773 ± 271 | 625 ± 219 | 99 ± 31 | 32 ± 10 | 756 ± 260 |
| Relative $AUC_{(0-6\ H)}$ | 240 ± 34 | 42 ± 9 | 14 ± 2 | 296 ± 45 | 104 ± 37 | 17 ± 5 | 5 ± 2 | 126 ± 44 |
| Total $AUC_{(0-24\ H)}$ | 1963 ± 436 | 364 ± 129 | 127 ± 52 | 2454 ± 617 | 1524 ± 832 | 280 ± 146 | 74 ± 27 | 1878 ± 978 |
| Relative $AUC_{(0-24\ H)}$ | 82 ± 18 | 15 ± 5 | 5 ± 2 | 102 ± 25 | 63 ± 34 | 12 ± 6 | 3 ± 1 | 78 ± 41 |

Discussion

At present, there is a weight of evidence supporting the beneficial effects of curcuminoids for the treatment of conditions associated with excessive inflammation and oxidative stress. However, curcumins traditionally poor oral bioavailability has limited its use. Numerous strategies have been developed to improve the bioavailability of this agent including cyclodextrin complexes, self-nanoemulsifying drug delivery systems, nanoparticle colloidal dispersions and nano-conjugates. Given the variance in both the delivery technique and method used to quantify in vivo curcumin, it is difficult to compare many of the findings reported in the literature. As such, no strategy has emerged superior for the enhancement in bioavailability of orally delivered curcumin.

The described trial was conducted under standardized conditions with the aim of controlling exogenous curcuminoids both prior to, and during the investigation. Consistent with similar research, baseline concentrations were essentially zero in both the test product and the standardised curcumin, thus we can confidently say there were no significant between group differences in plasma curcuminoids prior to dosage. CWD 90 with LipiSperse elicited the greatest increase in total plasma curcuminoid concentration, boasting a 3-fold improvement over the standard curcumin product. By attaching itself to the surface of curcumin particles, LipiSperse acts as a dispersing agent to lower the hydrophobicity of curcuminoids.

The trial demonstrated that 750 mg of curcuminoids combined with the LipiSperse delivery system could increase plasma curcuminoid concentration by 807 ng/mL above baseline. Other delivery techniques have been unable to match the efficacy of the dispersion system used in the present trial.

EXAMPLE 3

Liquid Dispersible Compositions Comprising Coenzyme Q10

Batch# CoQ10BT20170410_01 was prepared with 180.66 g of powdered coenzymeQ10 and 17.96 g of a dispersing agent prepared with 62.5% (w/w) hydrogenated ethoxylated castor oil, 25% (w/w) polyethylene glycol 400 and 6.25% (w/w) coconut oil. The coenzymeQ10 and dispersing agent were combined with high shear mixing with continuous grinding using a mortar and pestle.

A sample of the resulting composition was assayed for particle size by Particle & Surface Sciences Pty Ltd (Gosford, AUST). The mean particles size was 45.6 µM.

EXAMPLE 4

Liquid Dispersible Compositions Comprising Quercetin

Batch# B120170406_01 Quercetin CWD85 was prepared with 12.75 g of quercetin extract and 2.25 g of a dispersing agent prepared with 62.5% (w/w) hydrogenated ethoxylated castor oil, 25% (w/w) polyethylene glycol 400 and 6.25% (w/w) coconut oil, and 0.46 g of Silica colloidal anhydrous. The extract, silica and dispersing agent were combined with high shear mixing using continuous grinding with a mortar and pestle.

Figure 13:
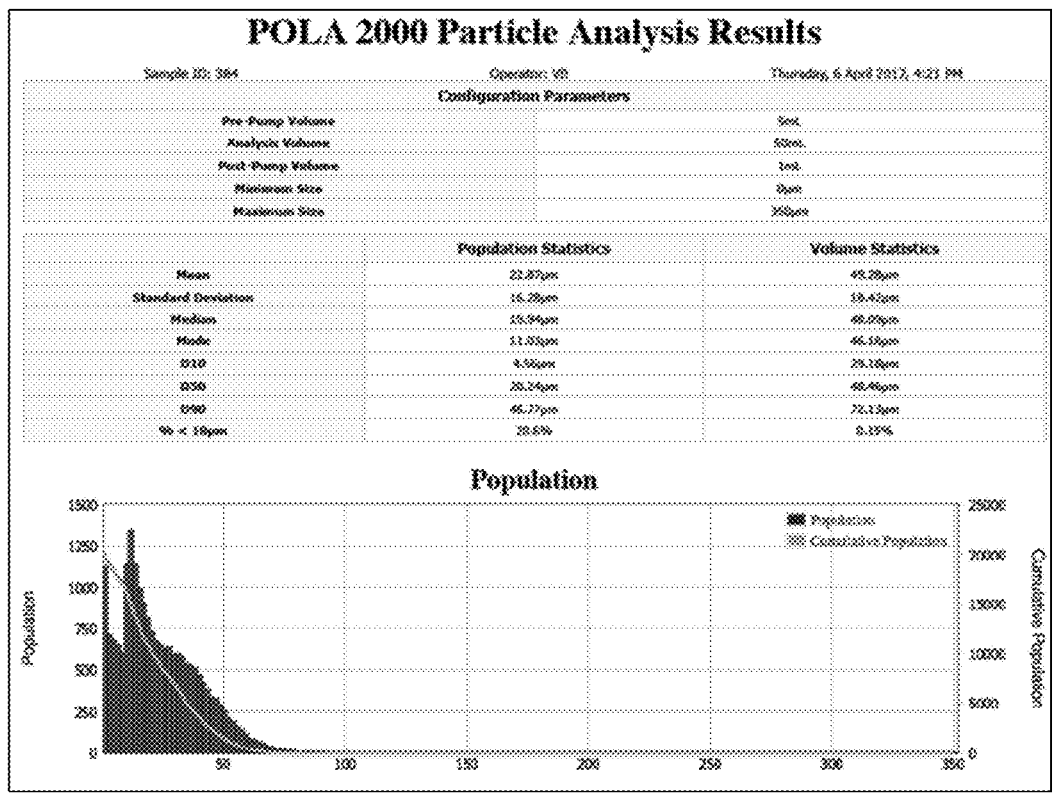
FIG. 13: Particle analysis results for Batch# BT20170406_01 Quercetin CWD85.

A sample of the resulting composition was assayed for particle size by Particle & Surface Sciences Pty Ltd (Gosford, AUST) (FIG. 13). The mean particles size was 22.87 µM.

EXAMPLE 5

Liquid Dispersible Compositions Comprising Resveratrol

Batch# Resveratrol CWD85BT20170405_3 was prepared with 18.6 g of resveratrol extract and 2.64 g of a dispersing agent prepared with 62.5% (w/w) hydrogenated ethoxylated castor oil, 25% (w/w) polyethylene glycol 400 and 6.25% (w/w) coconut oil, and 0.65 g of Silica colloidal anhydrous. The extract, silica and dispersing agent were combined with high shear mixing with continuous grinding using a mortar and pestle.

Figure 14:
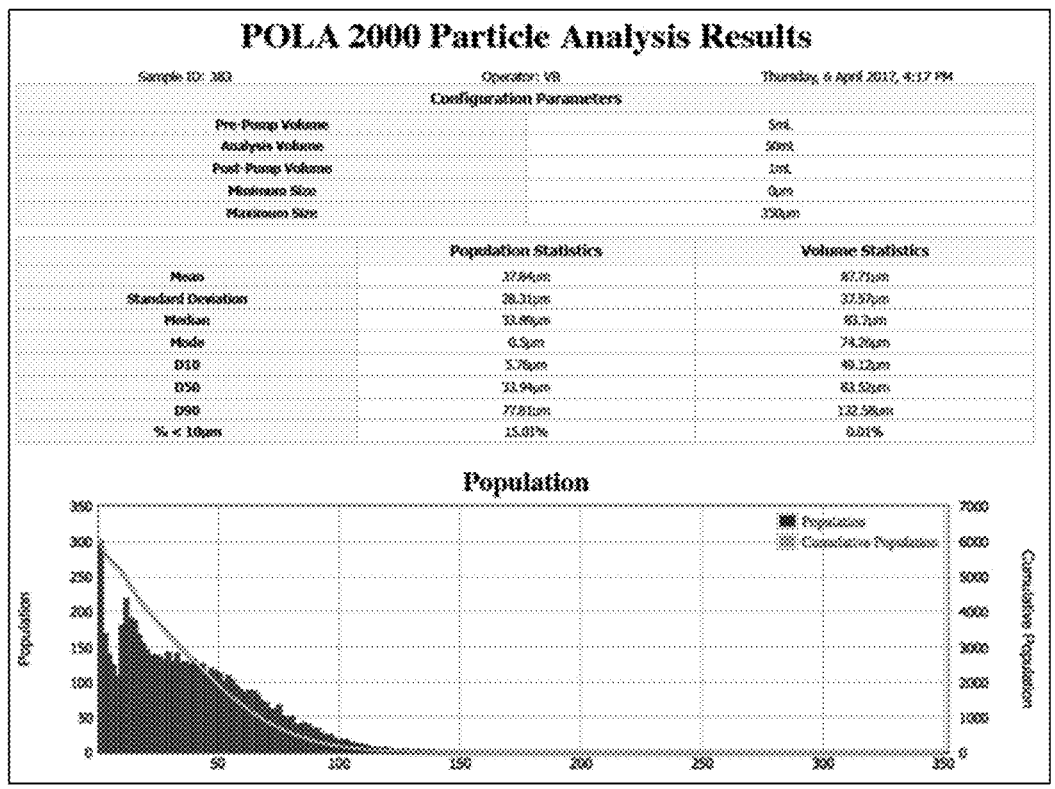
FIG. 14: Particle analysis results for Batch# Resveratrol CWD85BT20170405_3.

A sample of the resulting composition was assayed for particle size by Particle & Surface Sciences Pty Ltd (Gosford, AUST) (FIG. 14). The mean particles size was 37.94 µM.

Batch# Resveratrol CWD90 BT20170629_02 was prepared with 92.07 g of resveratrol extract and 7.09 g of a dispersing agent prepared with 70% (w/w) hydrogenated ethoxylated castor oil, 12.5% (w/w) polyethylene glycol 400 and 4.98% (w/w) olive oil, 12.5% (w/w) lime oil, 0.02% (w/w) lecithin, 0.02% (w/w) vitamin E acetate, and 1.084 g of Silica colloidal anhydrous. The extract and dispersing agent were combined with high shear mixing over two hours using a continuously rotating drum mixer in a plastic bottle with 8×20 mM metal ball bearings.

Figure 15:
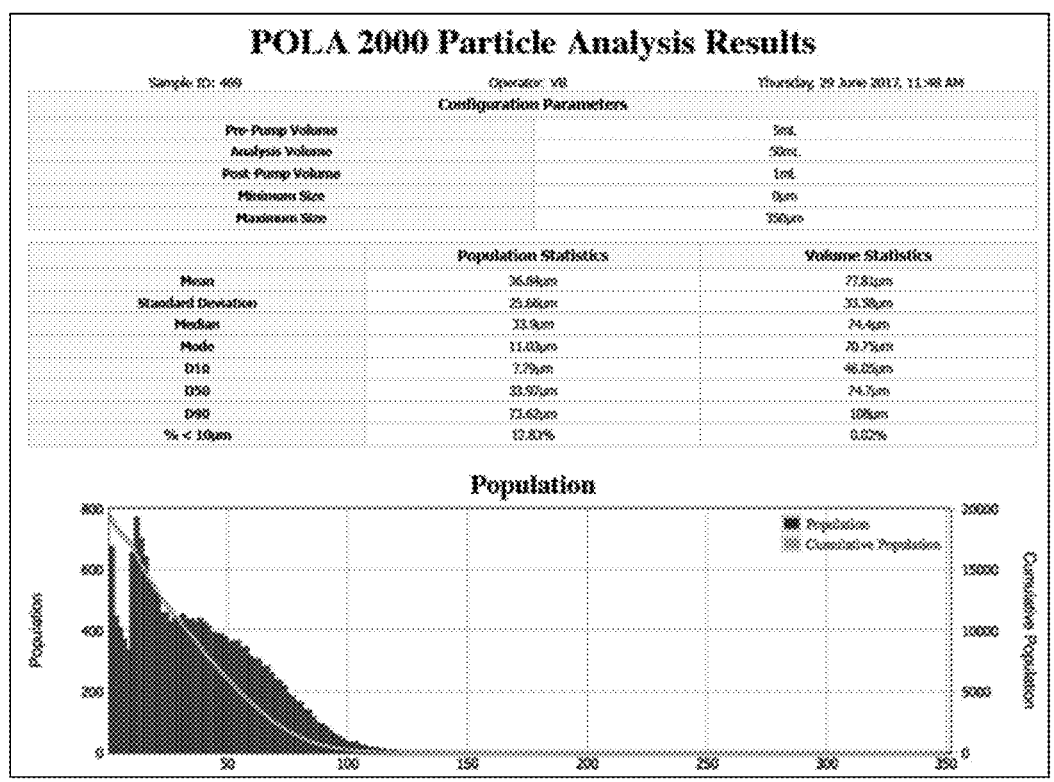
FIG. 15: Particle analysis results for Batch# Resveratrol CWD90 BT20170629_02.

A sample of the resulting composition was assayed for particle size by Particle & Surface Sciences Pty Ltd (Gosford, AUST) (FIG. 15). The mean particles size was 36.84 µM.

EXAMPLE 6

Liquid Dispersible Compositions Comprising Resveratrol

Batch# Resveratrol CWD 90 M120180228_06 was prepared with approximately 90% (w/w) resveratrol extract and approximately 9% (w/w) dispersing agent prepared with 70% (w/w) hydrogenated ethoxylated castor oil, 12.5% (w/w) polyethylene glycol 400 and 4.98% (w/w) olive oil, 12.5% (w/w) lime oil, 0.02% (w/w) lecithin, 0.02% (w/w) vitamin E acetate, and approximately 1% (w/w) Silica colloidal anhydrous. The extract was mixed with an impeller speed of 150 rpm and chopping blade speed of 2000 as the dispersing agent was spray added over 3 minutes. The silica was then added to the extract and dispersing agent and mixed with an impeller speed of 150 rpm and a cutting blade speed of 2000 rpm cutting blade speed for another 2 min.

Figure 16:
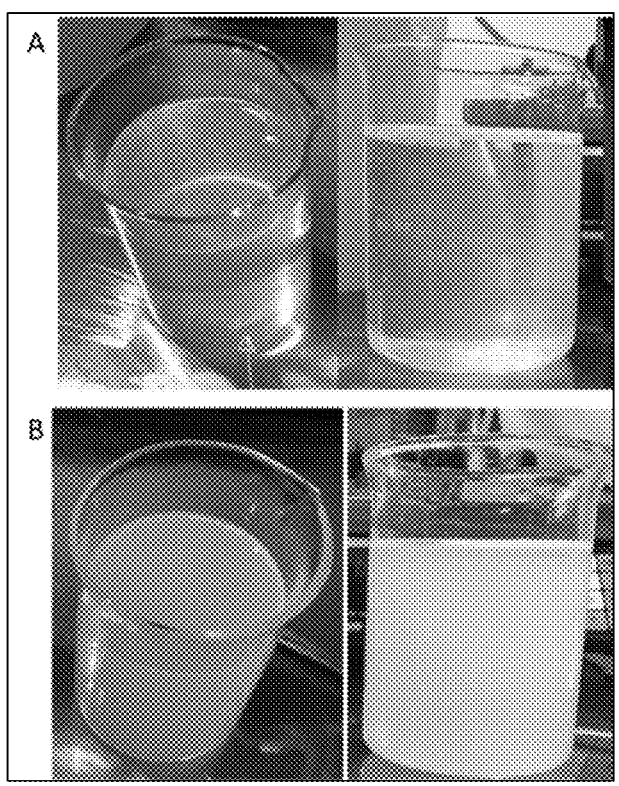
FIG. 16: Dispersion of sample of Batch# Resveratrol CWD 90 MT20180228_06 (Panel B at mixing (left) and after 3 minutes (right)), compared to untreated resveratrol (Panel A).

A sample of the composition was added to water and mixed and allowed to stand. FIG. 16 shows that the composition comprising the resveratrol prepared by the method of the invention (Panel B) remains dispersed after 3 min, while the untreated resveratrol does not disperse effectively (Panel A).

EXAMPLE 7

Liquid Dispersible Compositions Comprising PEA

Batch#MT20170615_01 was prepared with 9.39 kg of PEA and 0.61 kg of a dispersing agent prepared with 97% (w/w) Etocas 35, 0.5% (w/w) medium chain triglycerides, 0.5% (w/w) lime oil, 0.5% (w/w) olive oil, 0.5% (w/w/) vitamin E acetate, 0.5% (w/w) lecithin and 0.5% (w/w) oat oil, and 0.1 kg of Silica colloidal anhydrous. The extract was mixed with an impeller speed of 150 rpm and chopping blade speed of 2000 as the dispersing agent was spray added over 5 minutes. The silica was then added to the extract and dispersing agent and mixed with an impeller speed of 150 rpm and a cutting blade speed of 2000 rpm cutting blade speed for another 5 min, and repeated.

Figure 17:
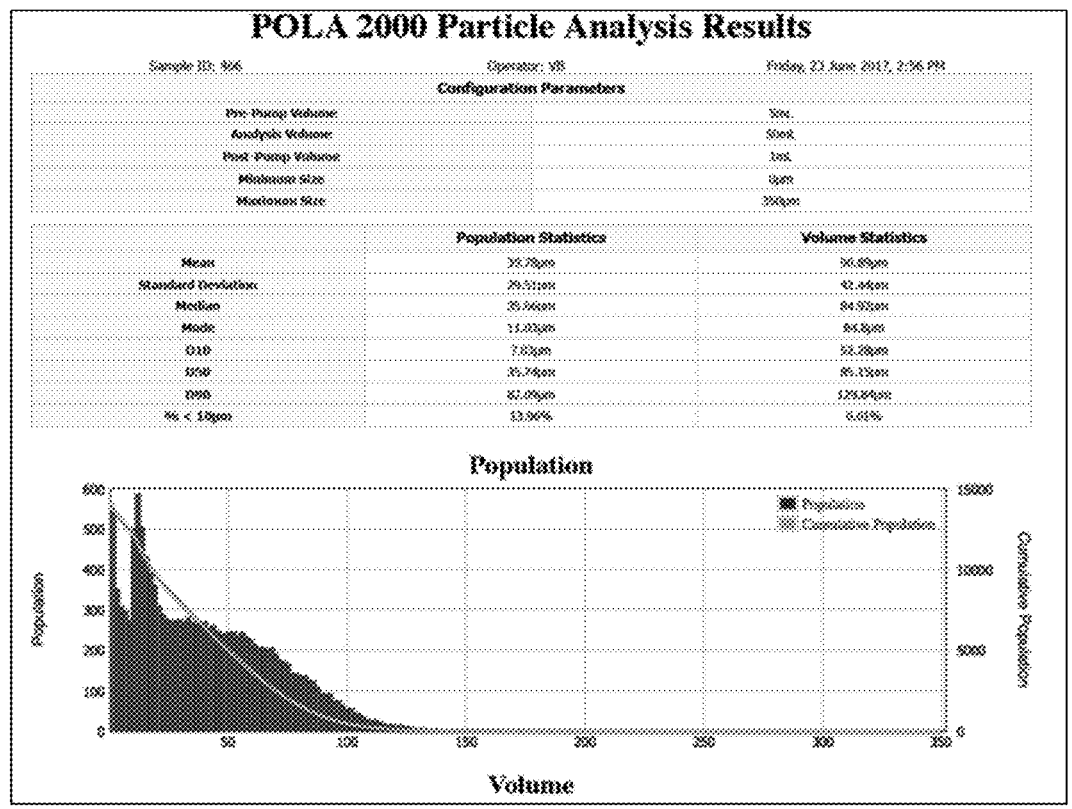
FIG. 17: Particle analysis results for Batch#MT20170615_01.
Figure 18:
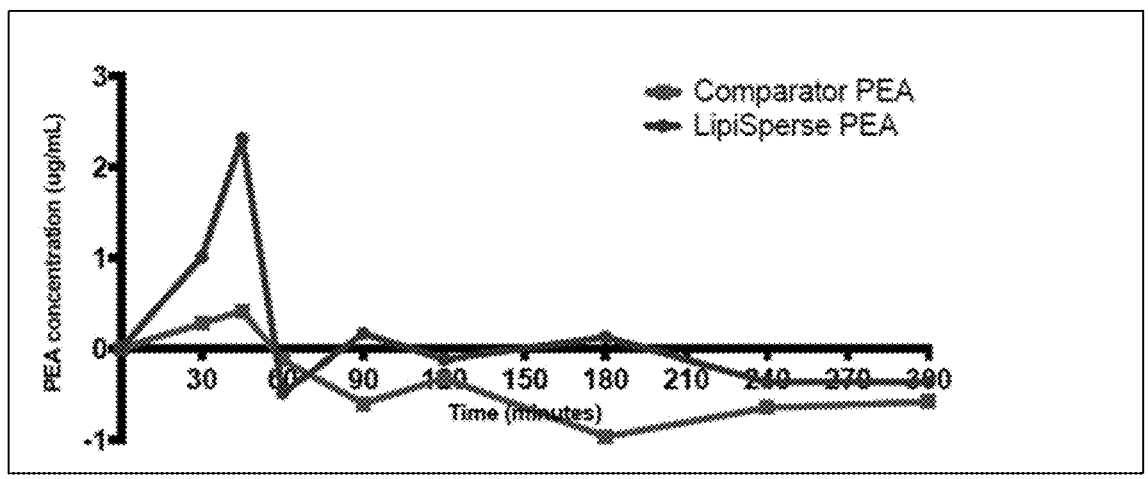
FIG. 18: Change in PEA concentration over 6 hours.

A sample of the resulting composition was assayed for particle size by Particle & Surface Sciences Pty Ltd (Gosford, AUST) (FIG. 17). The mean particles size was 39.78 µM.

EXAMPLE 8

Enhance Bioavailability of Liquid Dispersible Composition Comprising Curcumin

Palmitoylethanolamide (PEA) also known as N-(2-hydroxyethyl) hexadecanamide or N-(2-hydroxyethyl)-palmitamide is an endogenous saturated fatty acid derivative. PEA has been widely studied for its anti-inflammatory andanalgesic properties. It is reported PEA acts by down regulating mast cell degranulationat local sites and therefore exerts an antagonistic action against inflammation and pain receptor stimulation.

Study Parameters

A single equivalent dose, randomised, double blinded study was used to evaluate the pharmacokinetics of 2 different PEA formulations administered in single 300 mg doses (standard PEA and Lipisperse PEA from Batch#MT20170615_01 described in Example 7). All trial participants, investigators conducting the trial and the biochemist analysing the samples were blinded to who was on each product.

Subjects were healthy adult male (n=10) and female (n=8; non-pregnant and non-lactating) volunteers between the ages of 18-30 years. All participants were advised to fast from 10:00 μm the night prior to the study commencing until the collection of the first blood sample. Breakfast and lunch were provided to the participants at the centre. This is a standard feeding study with nutritionally balanced meals and snacks provided during the 0-6 hour sample collection. Subjects remained on site for the full 6 hours of sample collection. Only participants who provided at least 9 of the 11 samples collected between 0-24 hours had their data analysed.

Bioanalysis

For PEA pharmacokinetic analysis, blood samples (3mL collected into ethylenediaminetetraacetic acid (EDTA) containing tubes) were drawn prior to supplementation (hour 0) and at 30, 45, 60, 90, 120, 180, 240, 300, 360 minutes and 24 hours post supplementation. Once obtained, the blood collection tube was briefly mixed by inversion, placed on ice and centrifuged within 10 minutes of collection (600×g, 4° C. for 10 minutes) to separate the plasma. Once spun, EDTA plasma was carefully removed and approximately 3×500 μl aliquots made. Aliquots were temporarily stored at −20° C. (<48 hours) before being transported and stored at −80° C.

Sample Preparation

Plasma samples were removed from storage at −80° C. and allowed to thaw to room temperature. Once thawed, 100 μL of sample was added to a microfuge tube along with 20 μL of an internal standard solution (50 ng/mL of D8-arachidonic acid (D8-AA) in ethanol). Proteins were precipitated by adding 100 μL of acetone. The tubes were capped and vortex mixed for 15 seconds then put on ice for 10 minutes. The resulting solution was spun at 12,000×g for 10 minutes before the supernatant was removed into a new tube. To the supernatant, 800 μL of a methanol/chloroform solution (2:1) was added along with 240 μL of 3M HCl to achieve phase separation. This solution was vortex mixed for 10 seconds followed by gentle mixing on rotator. After 10 minutes of gentle rotation, the tubes were centrifuged at 12,000×g for 10 minutes with the resulting chloroform layer (bottom layer) transferred to a glass culture tube and dried under a stream of nitrogen gas.

Once dry, the samples were reconstituted in 100 μL of ethanol, mixed and the contents transferred to salinized GC-MS glass inserts and dried under nitrogen. Once dry, the samples were derivatized via the addition of 40 μL of pentafluorobenzylbromide (PFBBr, 10% in acetonitrile −4 μL of PFBBr and 36 μL of ACN) and 20 μL di-isopropylethylamine (DIPEA, 10% in acetonitrile–2 μL DIPEA and 18 μL of ACN) and vortex mixed for 5 seconds. Samples were then incubated at room temperature for 30 min before being dried under nitrogen and the insert placed into GC-MS vials. To each vial, 10 μL of anhydrous pyridine and 20 μL of bis-(trimethylsilyl)trifluoroacetamide and trimethylchlorosilane (BSTFA+TMCS, 99:1) was added, the vial capped and vortex mixed for 5 seconds. The samples were incubated for 20 min at 45° C. The samples were allowed to cool before 70 μL of anhydrous hexane was added and the samples place on the auto sampler rack for analysis.

The standard PEA was purchased from Sigma Aldrich (P0359-10MG) and stored at −20° C. as per manufacturer's instructions. The PEA standard was made up to 1 mM solution with ethanol. Working standard solutions were prepared by diluting the 1 mM solution (or 1 μM/mL) 1:10 with ethanol for a 100 nM/mL solution. This solution was further diluted 1:10 with hexane for a concentration of 10 nM/mL. This constitutes our highest standard. The 10 nM/mL solution was subsequently diluted with hexane to give a 3 more standards with final concentrations of 5, 1 and 0.1 nM/mL. Ethanol was initially used as a diluent due to the concentration of PEA that can be dissolved into it. Hexane was later used as a diluent as it is better suited for GC-MS injections.

To account for the efficiency of the sample extraction process, an internal standard, D8-AA, was added to all plasma samples at the beginning of the extraction. The resulting recovered concentration was then compared to the same amount of D8-AA injected directly (100% value) to give the recovery percentage. The recovery percentage was then applied to the results to give the true concentration of PEA in the sample.

Analysis

The GC-MS method used for the analysis of samples was developed based on several existing method for PEA analysis. Samples were analyzed for PEA concentration using a Varian 320 MS/MS, with a Varian 450 gas chromatograph equipped with a CP8400 auto sampler.

Identification of the PEA peak in biological samples was made by running the pure PEA standard (Sigma) through the GC-MS in scan mode. The extracted samples were then run, and by overlaying the standards chromatogram with the extracted chromatograms, confirmation of the peak and elution time was made. Confirmation of the PEA peak was made at m/z 370.3. D8-AA was analysed in MS-MS mode with at m/z 311>266. No stable transition mass was able to be detected for PEA.

Pharmacokinetic parameters were derived using GraphPad Prism 7. Using the average PEA concentration data from each group we analysed for: AUC for the total PEA concentration and change in PEA concentration, the time for PEA concentration to peak and the peak change in PEA concentration from baseline.

Results 18 people were recruited for this study (n=9 per group), with all participants completing the study. Group 1—Lipisperse PEA (n=9, age 27.4±4.8) and Group 2—Standard PEA (n=9, age 29.2±4.7). No adverse events were reported during the study.

The PEA concentration in biological samples was calculated using a 4 point standard curve and the Varian quantification software for the GC-MS/MS. All samples fell within the range of the linear standard curve. The intra-assay precision CV was 4.8% and the inter-assay variability and precision CV was 7.3%.

Figure 1:
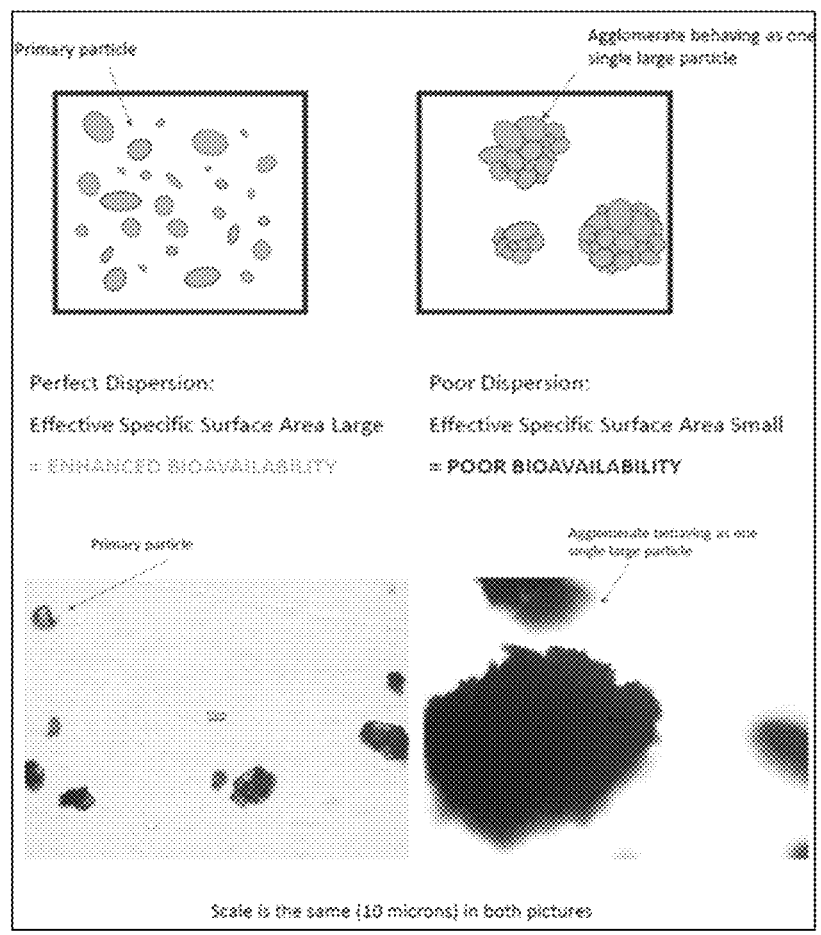
FIG. 1: Comparison of dispersion and effect on bioavailability. Bottom left is an SEM image of a composition comprising curcumin prepared by the method of the invention, and bottom right is curcumin alone.
Figure 2:
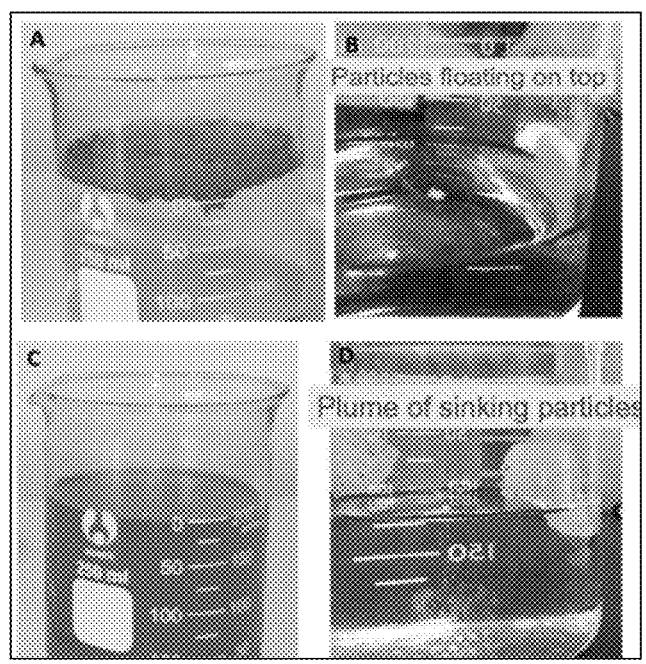
FIG. 2: Demonstration of liquid dispersibility. Panels A and B show solid substances (curcumin and PEA, respectively) with poor wettability sitting on top of a liquid, without dispersion. Panels C and D show the same solid substances, after being treated by the method of the present invention, penetrating the water.
Figure 3:
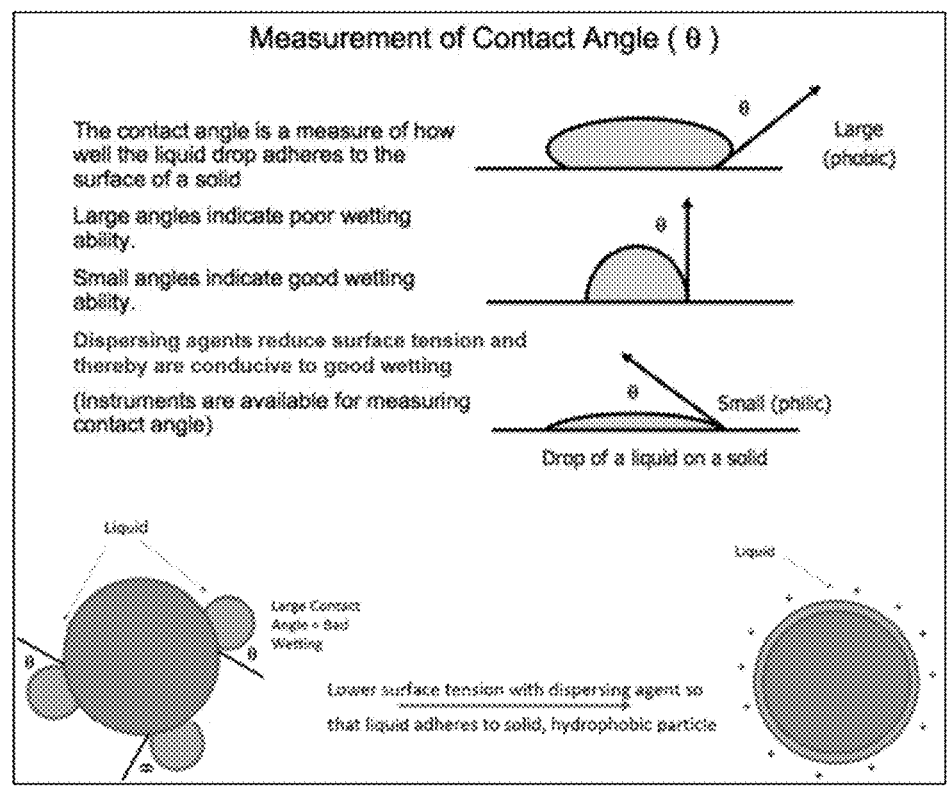
FIG. 3: Schematic showing relation between contact angle and wettability, and the dispersing agents of the present invention.

Following the quantification of PEA, the change in PEA concentrations due to supplementation was plotted (FIG. 1). PEA concentration at baseline was similar between the two groups. Results are summarized in Table 3 below.

TABLE 3

PEA concentrations for both groups. Total AUC is calculated on the PEA concentration change from baseline data.

|  | Group 1 Lipisperse PEA 300 mg | Group 2 Standard PEA 300 mg |
|---|---|---|
| Baseline | 1.99 ± 0.56 | 2.59 ± 0.77 |
| $C_{max}$ | 4.31 ± 3.02*# | 3.01 ± 1.24 |
| Delta $C_{max}$ | 2.31 | 0.41 |
| Peak timing (min) | 45 | 45 |
| Total $AUC_{(0-6\ h)}$ | 147.9# | 85.8 |

All values are in µg/mL,
*Significant compared to baseline value in the same group,
Significant compared to standard PEA group.
p < 0.05.

Following supplementation, both groups experienced an increase in plasma PEA concentration above baseline. However, only the Lipisperse PEA (Batch#MT20170615_01) group showed a significant increase above baseline concentrations (p<0.05). Lipisperse PEA also significantly increased PEA concentration (p<0.05) when compared to the standard PEA formulation. The kinetic profiles of the products shows a single peak plasma concentration-time course over the 24 hours (24 hour data not shown). With maximum PEA concentration occurring 45 minutes after supplementation and concentrations returning to baseline levels 60 minutes after supplementation. Baseline concentrations were then maintained from 60 minutes in both the Lipisperse and standard formulation group up until, and including, the 24 hours collection (2.69±1.06 µg/mL and 2.69±1.06 µg/mL respectively; data not shown).

Discussion

PEA is an important molecule in the body and its potential benefits as a supplement has recently become evident. However, as the absorption of PEA is low, there has been the need to find ways to increase the absorption of PEA into the body. Studies have investigated technologies including nanoparticles, liposomes and other lipid based delivery systems, however, there are no known studies conducted in humans.

The results of this pharmacokinetic study presented here demonstrates that the novel dispersion system, Lipisperse, was able to increase the peak absorption of PEA more than 5 times that of a standard PEA product after a single oral administration of 300 mg.

Lipisperse PEA and standard PEA formulations both demonstrated an initial and rapid peak in plasma concentration 45 minutes post supplementation. This was followed by a rapid return to baseline within 60 minutes post supplementation. The rapid appearance and disappearance of PEA in the plasma supports the role of PEA as a potential compound in the treatment of pain and inflammation. After PEA concentrations returned to baseline values, there were no further increasing in PEA throughout the following 5 hours of collection or at 24 hours post supplementation. This indicates that the observed peak was a result of the supplementation and that the supplementation exceeded any possible diurnal effect or natural PEA increases.

The invention claimed is:

1. A method of preparing a liquid dispersible composition comprising a hydrophobic compound and a dispersing agent, the method consisting of combining a solid substance with the dispersing agent in the presence of an anti-caking agent whilst applying a shear force, wherein the solid substance comprises the hydrophobic compound and wherein a ratio of the solid substance and the dispersing agent in the composition is from about 10:1 to 9:1,
   wherein the dispersing agent consists of:
   50% (w/w)-79% (w/w) an amphiphilic molecule,
   1% (w/w)-10% (w/w) solvent,
   20% (w/w)-30% (w/w) carrier oil,
   at least one of lecithin, phosphatidylcholine, oat oil, or a polar lipid, and
   a preservative selected from the group consisting of ascorbyl palmitate, vitamin E, a vitamin E derivative, an olive polyphenol, and an algal polyphenol,
      wherein the dispersing agent comprises at least 20% (w/w) medium chain triglycerides as the carrier oil,
      wherein the amphiphilic molecule is at least one non-ionic surfactant,
   wherein the solvent is a citrus oil,
   wherein the hydrophobic compound is a curcuminoid being a powdered extract of Curcuma longa containing at least 95% (w/w) curcuminoid,
   wherein the composition, when mixed with water, produces a population of particles and greater than 50% of the population of particles are between 1 µm and 100 µm in diameter and wherein the method increases the bioavailability of the curcuminoid compared to a corresponding control.

2. The method of claim 1, wherein the at least one non-ionic surfactant is selected from the group consisting of: hydrogenated castor oil, macrogolglycerol hydroxystearate, poloxamer, polyoxyl 35 castor oil, polyoxyl 40 castor oil, polysorbate 20(Tween 20), polysorbate 60 (Tween 60), polysorbate 80 (Tween 80), polyglycerol polyricinoleate, D-alpha-tocopherol polyethylene glycol 1000 succinate (TPGS), polyglycerol esters of fatty acids, and glyceryl monooleate.

3. The method of claim 1, wherein the anti-caking agent is selected from the group consisting of a stearate of calcium, a stearate of magnesium, a silica-based agent, flour and starch.

4. The method of claim 1, wherein the bioavailability of the curcuminoid is at least 3-fold greater when compared to a corresponding curcuminoid control, wherein the bioavailability is determined by measuring blood plasma concentration of the curcuminoid in a subject following administration of a total dose of 750 mg of curcuminoid.

5. The method of claim 1, wherein the shear force is created by high-shear mixing and the high-shear mixing is achieved by milling, rotor-stator mixing, chopping, high-pressure homogenization or combinations thereof.

6. The method of claim 5, wherein said milling is ball milling, pin milling, jet milling, colloidal milling or grinding with a mortar and pestle.

* * * * *